US 6,562,628 B1

(12) United States Patent
Liu et al.

(10) Patent No.: US 6,562,628 B1
(45) Date of Patent: May 13, 2003

(54) ELECTROLYTIC SUPPRESSOR AND SEPARATE ELUENT GENERATOR COMBINATION

(75) Inventors: Yan Liu, Santa Clara, CA (US); Nebojsa Avdalovic, El Dorado Hills, CA (US); Hamish Small, Leland, MI (US)

(73) Assignee: Dionex Corporation, Sunnyvale, CA (US)

( * ) Notice: Subject to any disclaimer, the term of this patent is extended or adjusted under 35 U.S.C. 154(b) by 260 days.

(21) Appl. No.: 09/612,113

(22) Filed: Jul. 7, 2000

(51) Int. Cl.[7] .................. G01N 30/02; G01N 30/90; G01N 31/16; G01N 31/22; G01N 21/00; G01N 21/75
(52) U.S. Cl. .................................... 436/161; 422/70
(58) Field of Search .......................... 436/161; 422/70

(56) References Cited

U.S. PATENT DOCUMENTS

| | | |
|---|---|---|
| 4,999,098 A | 3/1991 | Pohl et al. |
| 5,045,204 A | 9/1991 | Dasgupta et al. |
| 5,248,426 A | 9/1993 | Stillian et al. |
| 5,352,360 A | 10/1994 | Stillian et al. |
| 5,407,553 A * | 4/1995 | Herron et al. ............ 204/636 |
| 5,633,171 A * | 5/1997 | Small et al. ............... 204/550 |
| 5,759,405 A | 6/1998 | Anderson, Jr. et al. |
| 6,017,433 A * | 1/2000 | Mani .......................... 204/524 |
| 6,027,643 A * | 2/2000 | Small et al. ............... 205/789 |
| 6,036,921 A * | 3/2000 | Small et al. ............... 204/551 |
| 6,093,327 A * | 7/2000 | Anderson et al. ......... 210/198.2 |
| 6,251,259 B1 * | 6/2001 | Satoh et al. ............... 204/229.6 |
| 6,296,751 B1 * | 10/2001 | Mir ............................ 204/524 |

FOREIGN PATENT DOCUMENTS

| | | |
|---|---|---|
| WO | 96/27793 | 12/1996 |
| WO | 99/11351 | 3/1999 |
| WO | 99/44054 | 9/1999 |

* cited by examiner

Primary Examiner—Jill Warden
Assistant Examiner—Jennine Brown
(74) Attorney, Agent, or Firm—Dorsey & Whitney LLP; David J. Brezner

(57) ABSTRACT

A combination electrolytic suppressor and separate eluent generator and method. The suppressor includes a chromatography effluent flow channel, an ion receiving flow channel, and a first suppressor ion exchange barrier therebetween permeable to electrolyte ions but not liquid flow. The effluent from the chromatography effluent compartment flows through the detector, the ion receiving channel, and to an eluent generator. The generator includes a first generator electrode in a first generator electrode chamber, an electrolyte ion reservoir, a first charged generator barrier separating the first eluent generator electrode chamber from the electrolyte ion reservoir, preventing liquid flow but permitting transport of said electrolyte ions, and a second generator electrode on the opposite side of the first generator barrier from the first generator electrode. Fluid flows from the ion receiving flow channel past the second generator electrode. Acid or base electrolytically generated in the first generator electrode chamber flows as an eluent stream to the chromatographic separator.

25 Claims, 11 Drawing Sheets

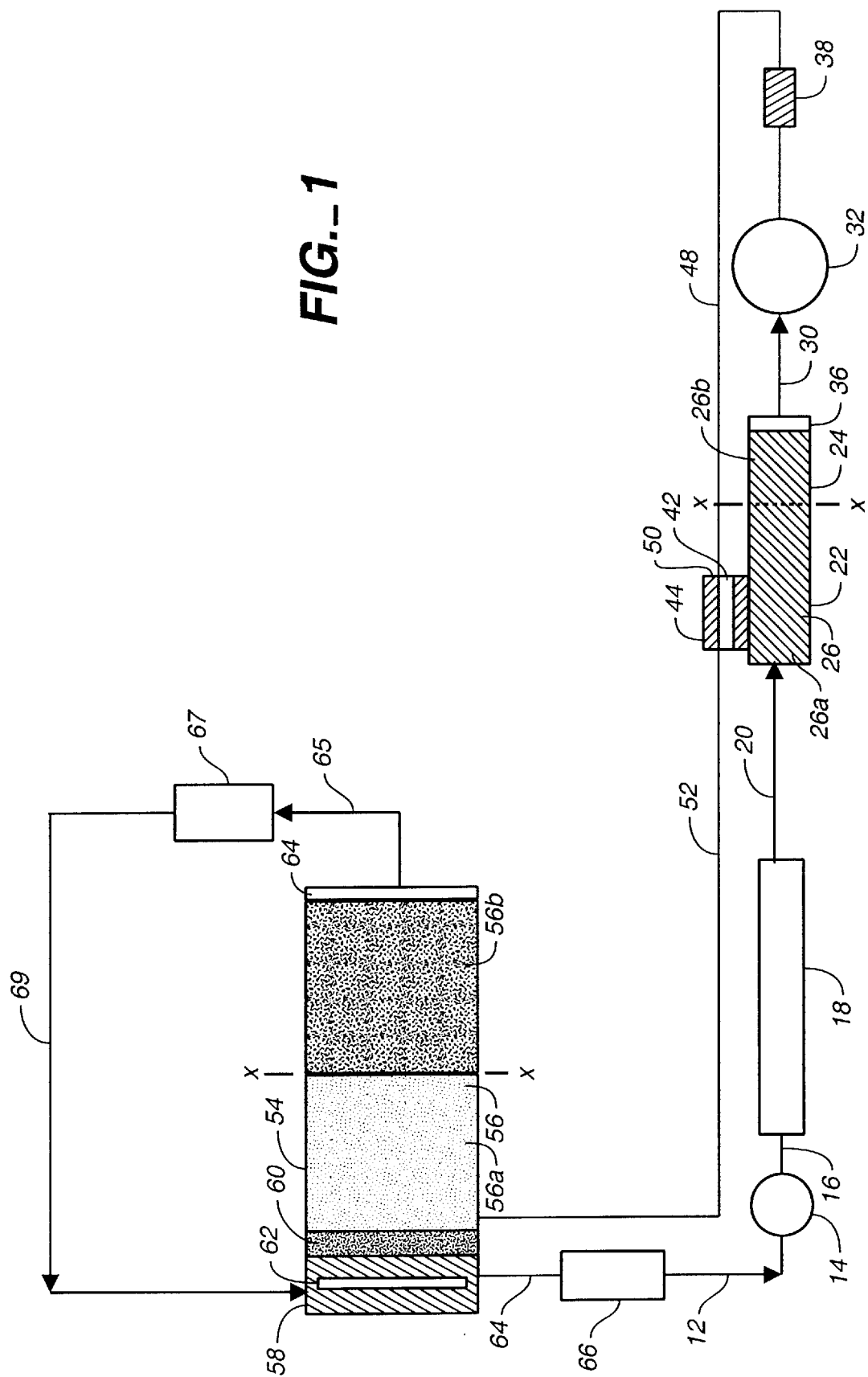
FIG._1

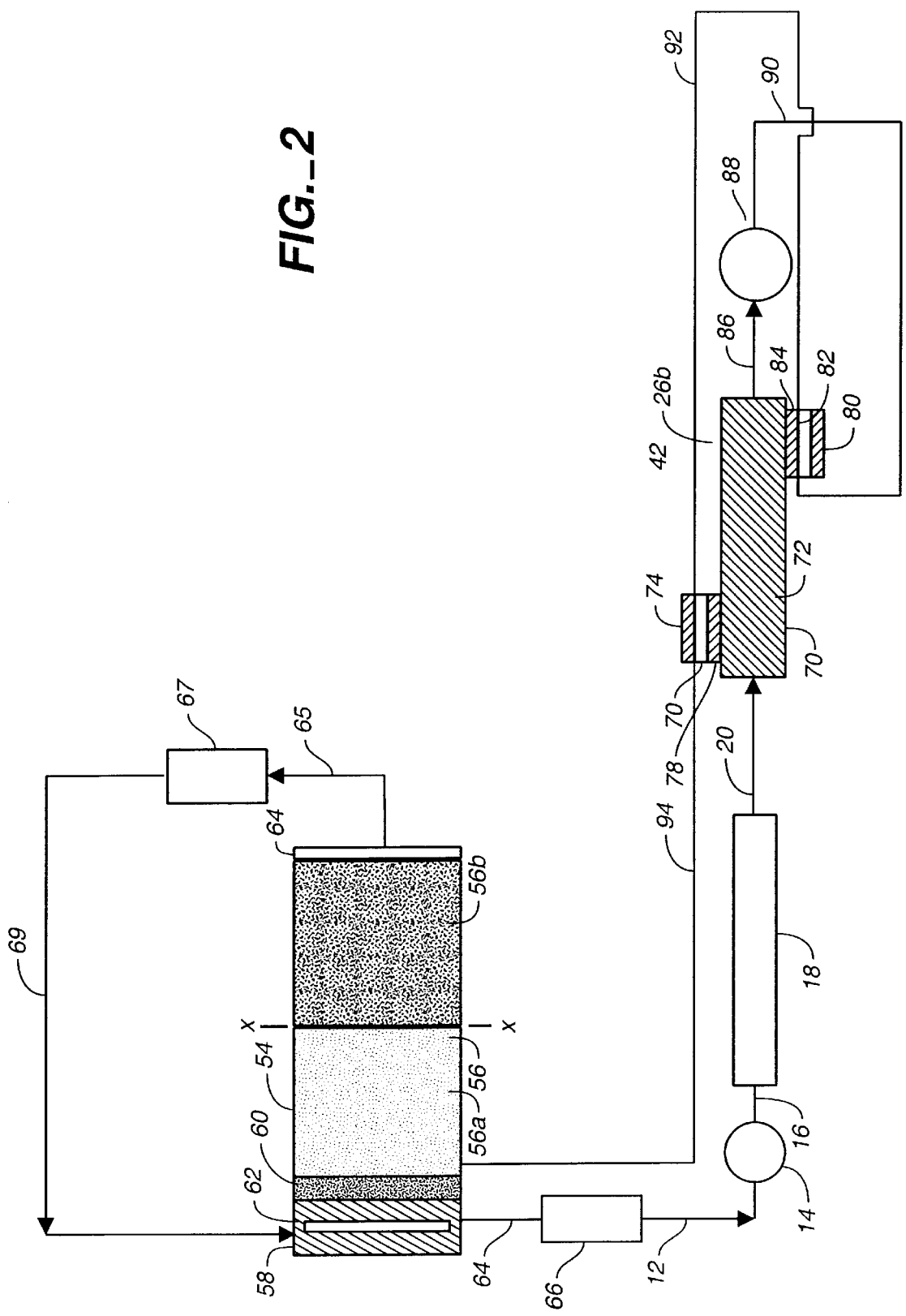
FIG._2

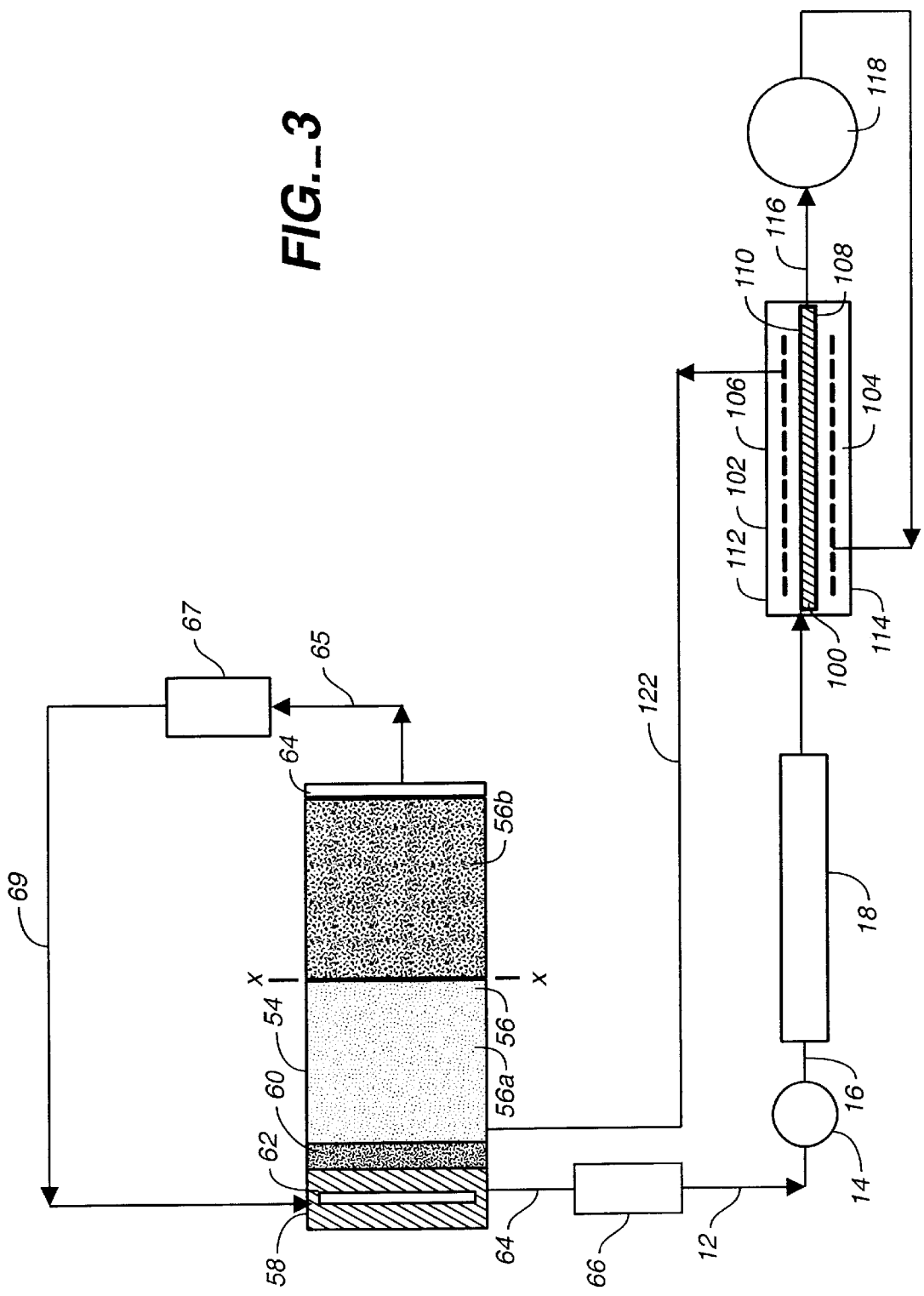

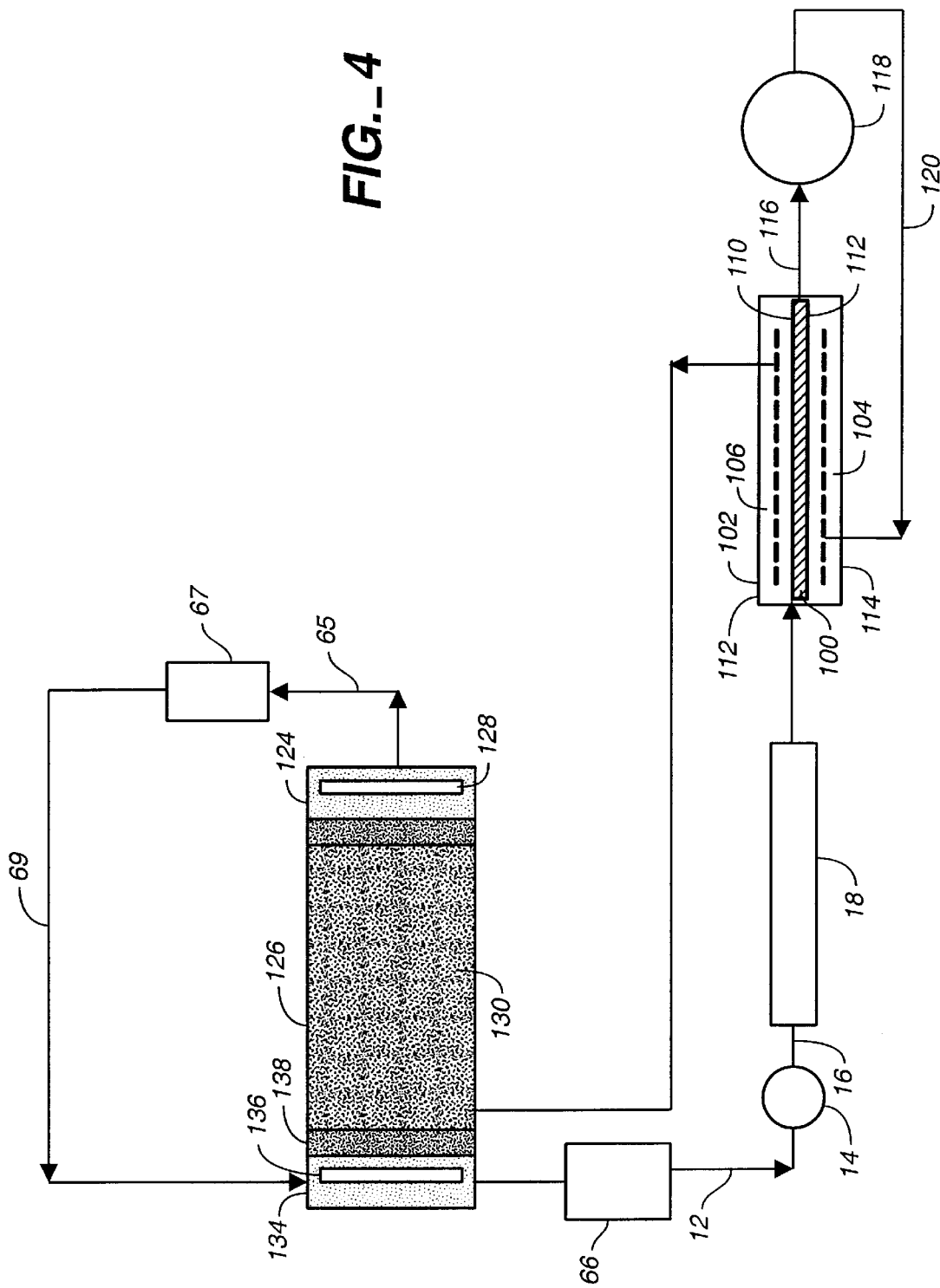
FIG._4

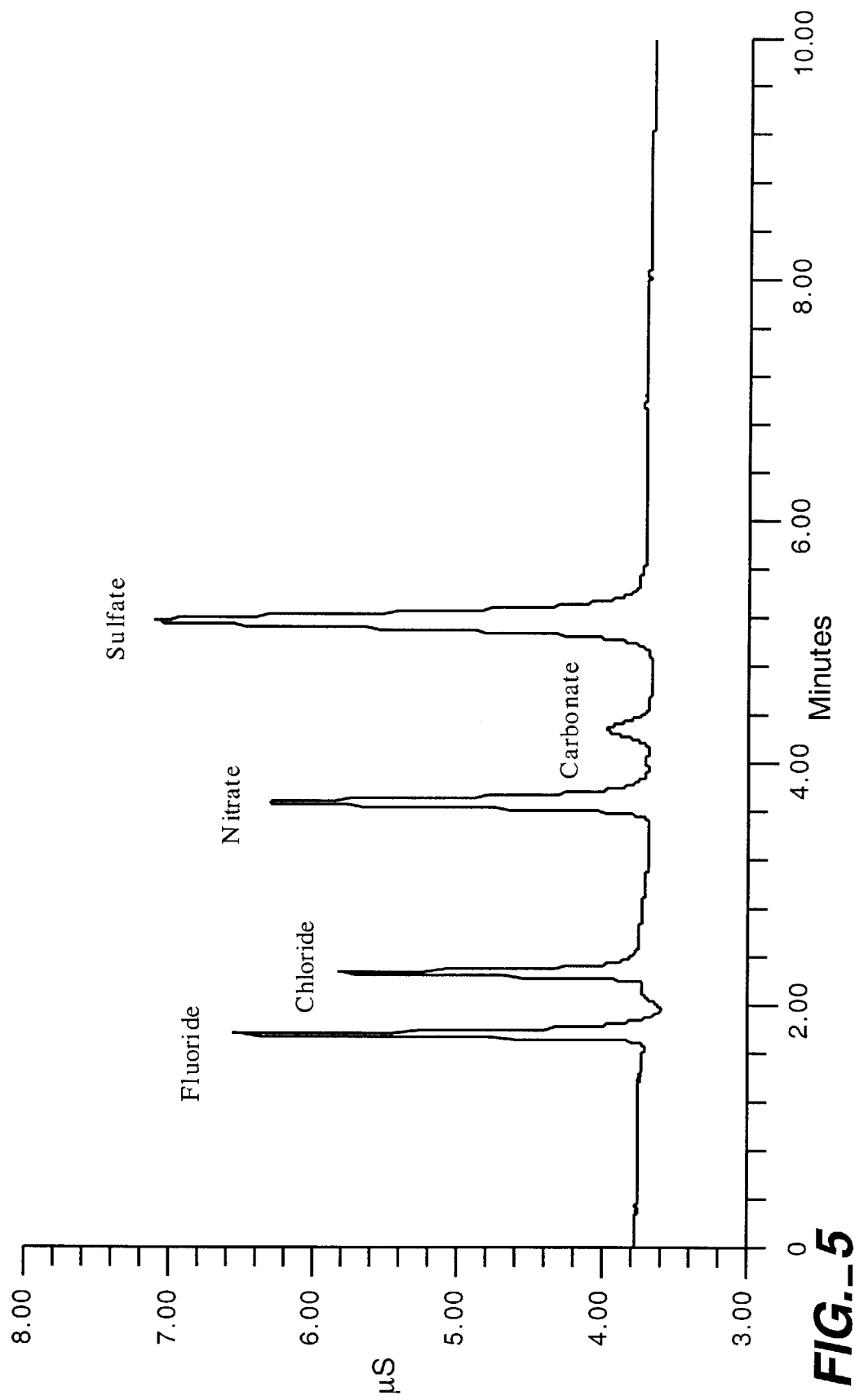
FIG._5

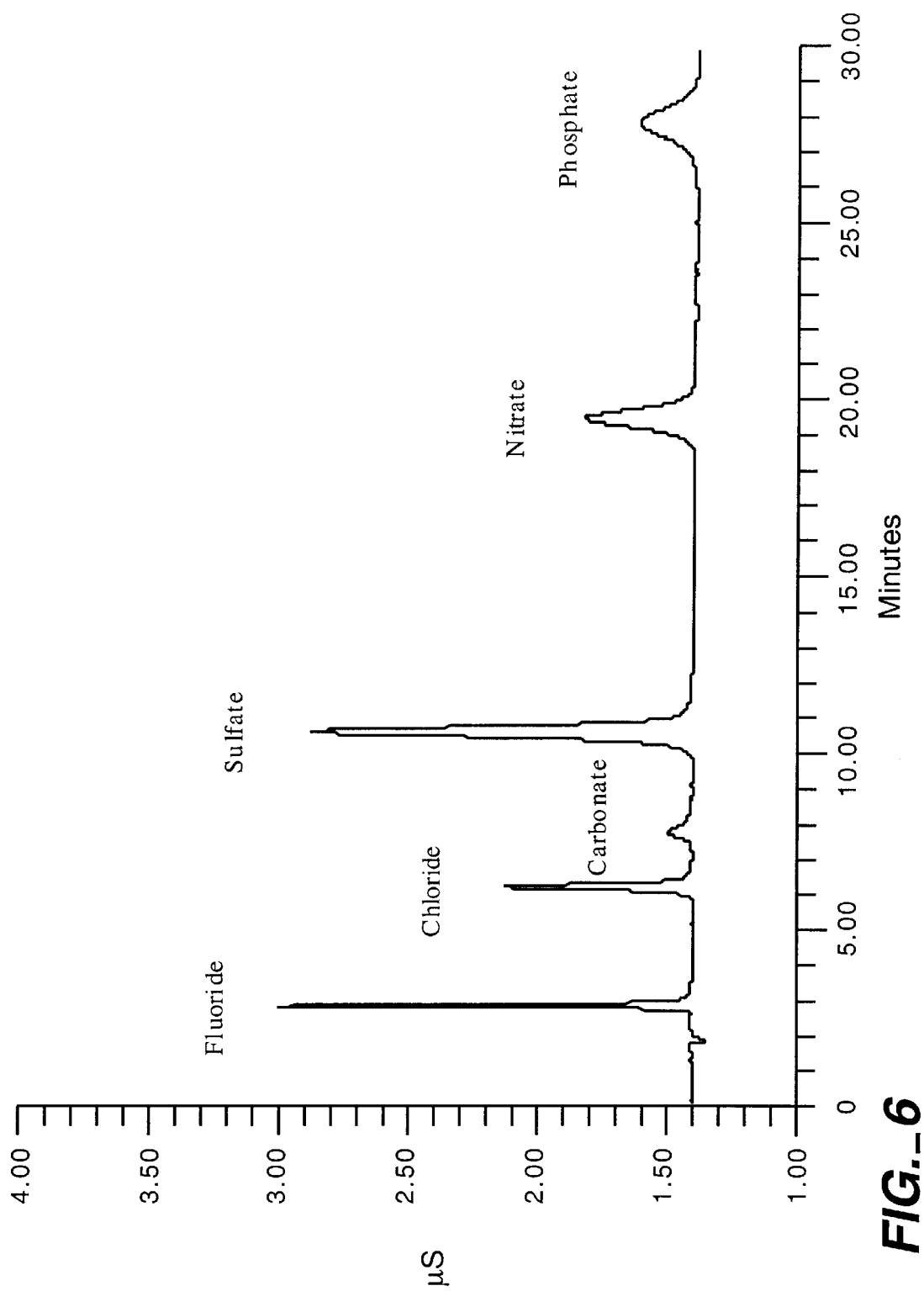
FIG._6

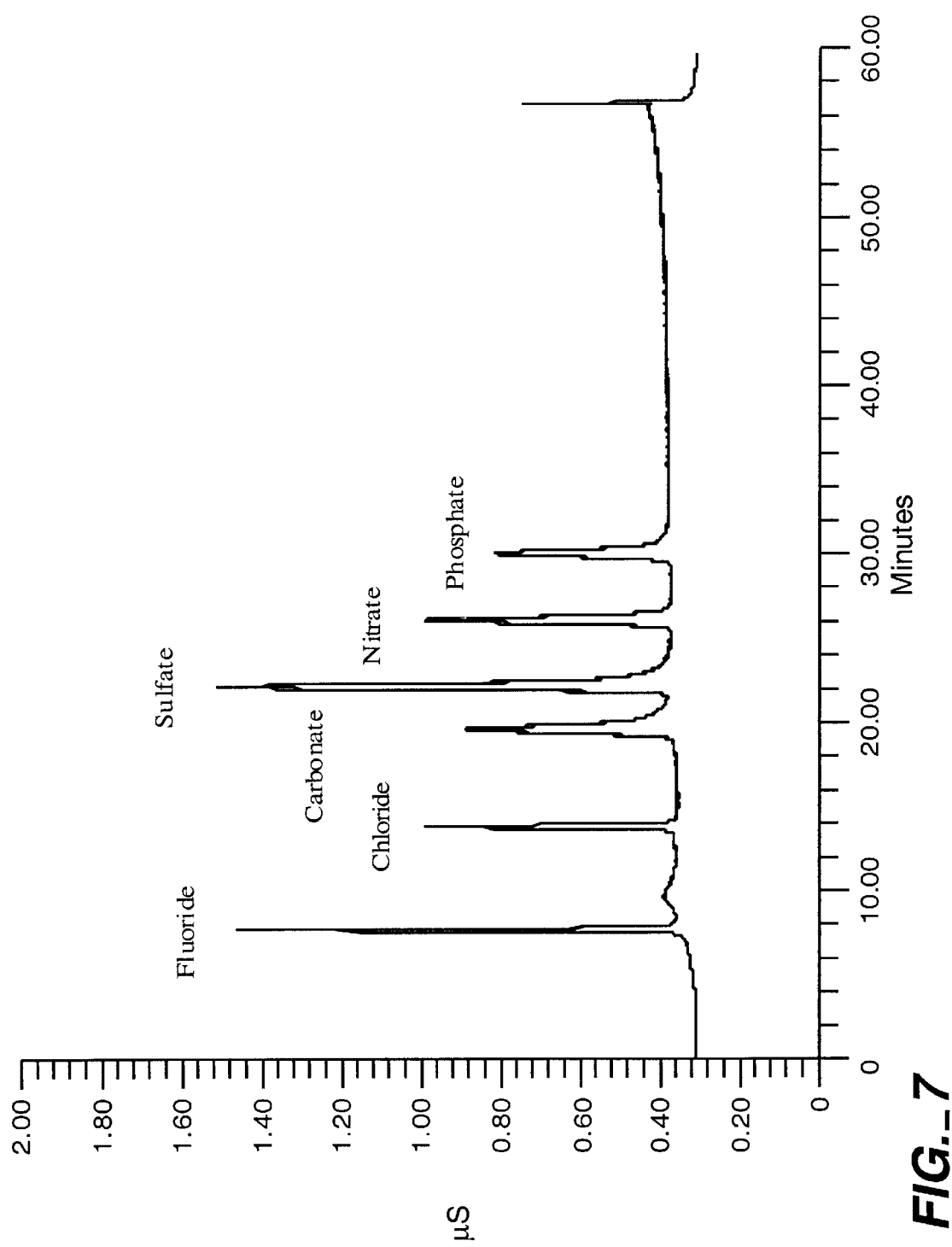
FIG._7

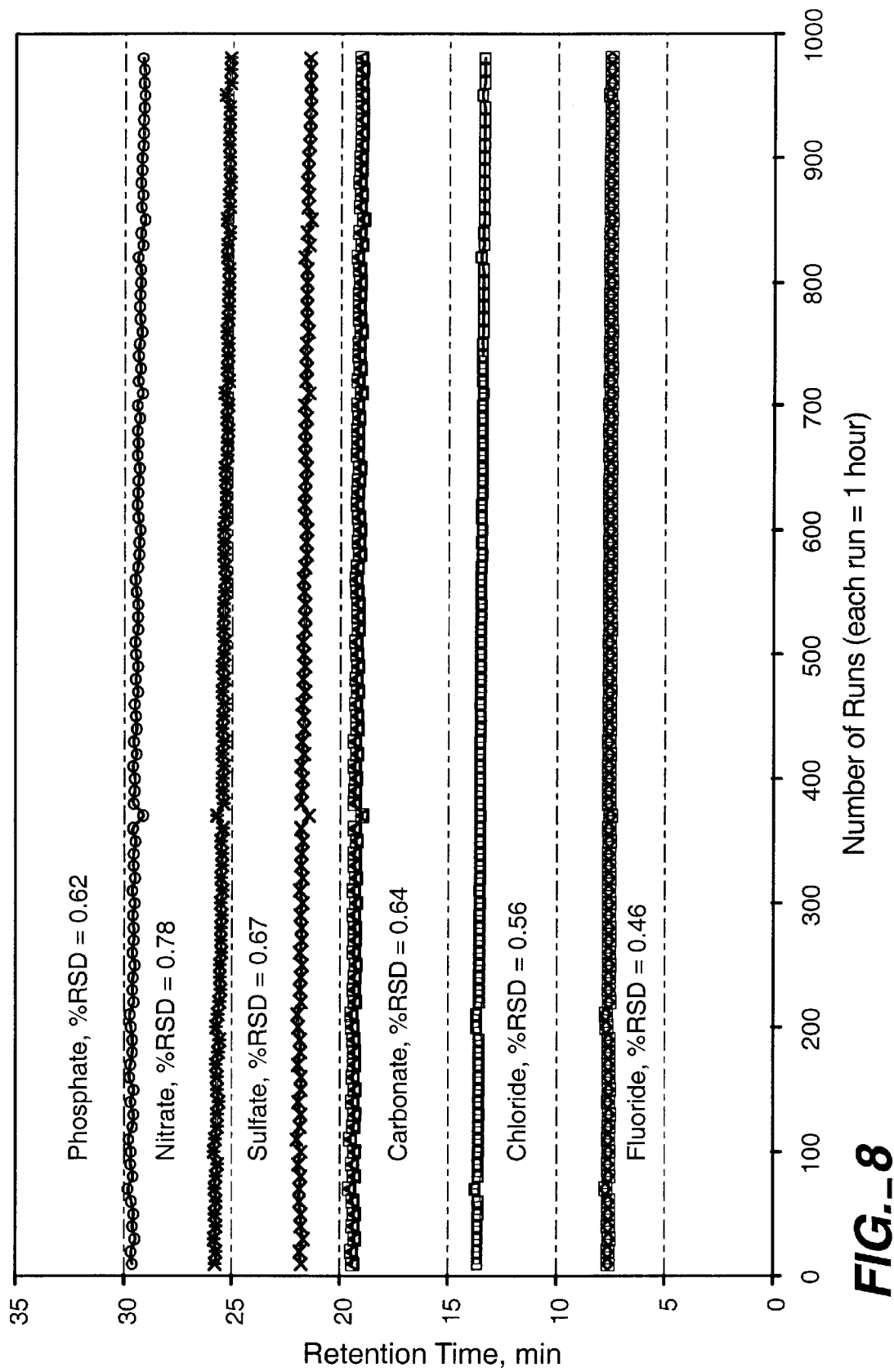
FIG._8

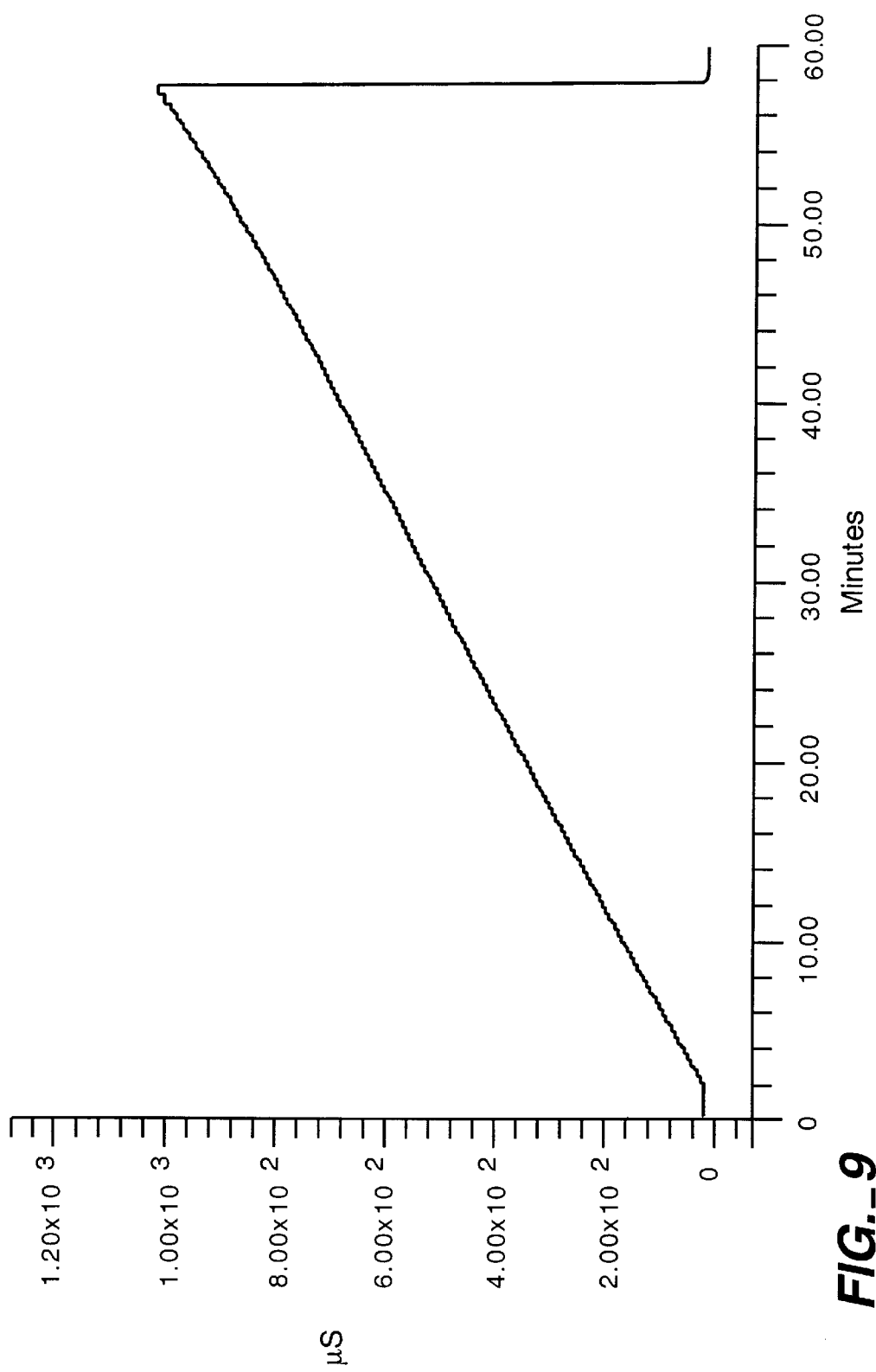
FIG._9

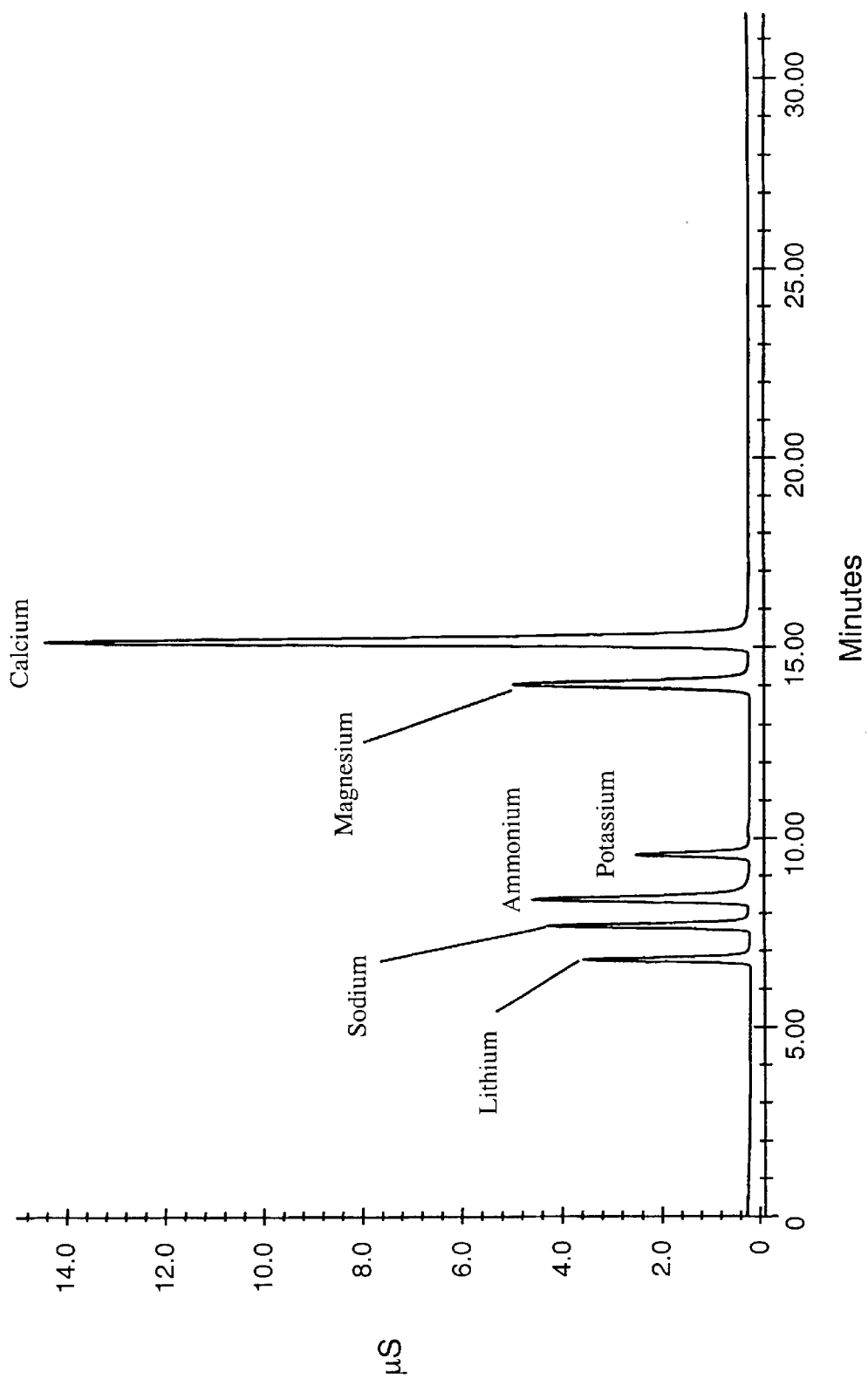
FIG._10

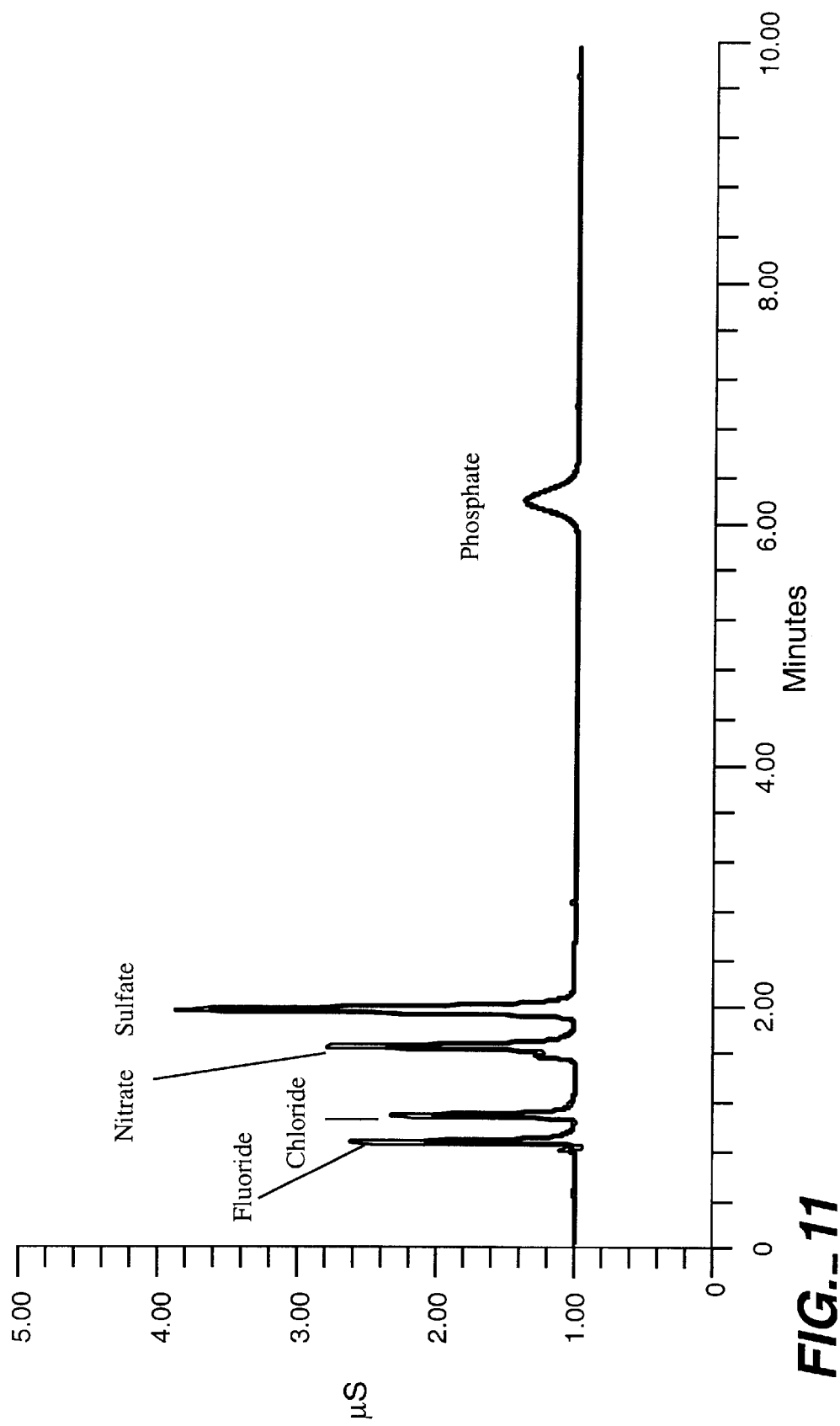
FIG._11

ELECTROLYTIC SUPPRESSOR AND SEPARATE ELUENT GENERATOR COMBINATION

BACKGROUND OF THE INVENTION

The present invention relates to method and apparatus using continuous electrolytic suppression of electrolyte in eluents particularly for the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,926,559.

Suppression or stripping of the electrolyte is described in the above prior art references by a bed of ion exchange resin particles commonly referred to as a packed bed suppressor (PBS). The PBS requires periodic regeneration by flushing with an acid or base solution.

One form of packed bed suppression uses intermittent electrolytic regeneration as described in U.S. Pat Nos. 5,633,171 and 5,759,405. An electrical potential is applied through the resin in the packed bed suppressor while flowing an aqueous liquid stream to electrolyze water in the stream. For the analysis of anions, a PBS containing fully sulfonated cation exchange resin is fitted with a cathode embedded in the resin at the suppressor inlet and an anode embedded in the resin at the suppressor outlet. Hydronium ions generated at the anode displace the sodium ions which associate with the hydroxide ions for passage to waste, in this instance through the conductivity cell. This process electrochemically regenerates the suppressor, and after the electrical potential is turned off, the device can be used as a conventional PBS.

A different form of a suppressor is described and published in U.S. Pat No. 4,474,664, in which a charged ion exchange membrane in the form of a fiber or sheet is used in place of a resin bed. The sample and eluent are passed on one side of the membrane with a flowing regenerant on the other side, the membrane partitioning the regenerant from the effluent of the chromatographic separation. The membrane passes ions of the same charge as the exchangeable ions of the membrane to convert the electrolyte of the eluent to weakly ionized form, followed by detection of the ions.

Another suppression system is disclosed in U.S. Pat. No. 4,459,357. There, the effluent from a chromatographic column is passed through flow channel defined by flat membranes on both sides of the channel. On the opposite sides of both membranes are channels through which regenerant solution is passed. As with the fiber suppressor, the flat membranes pass ions of the same charge as the exchangeable ions of the membrane. An electric field is passed between electrodes on opposite sides of the effluent channel to increase the mobility of the ion exchange.

In U.S. Pat. No. 4,403,039, another form of electrodialytic suppressor is disclosed in which the ion exchange membranes are in the form of concentric tubes. One of the electrodes is at the center of the innermost tube.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

Another improvement in suppression is described in U.S. Pat. No. 5,248,426. This form of suppressor was introduced as a commercial product in 1992 by Dionex Corporation under the name "Self Regenerating Suppressor" (SRS). A direct current power controller generates an electric field across two platinum electrodes to electrolyze water in the regenerant channels. Functionalized ion-exchange screens are present in the regenerant chambers to facilitate electric current passage with permselective ion-exchange membrane defining the chromatography eluent chamber, as in the '098 patent. After detection, the chromatography effluent is recycled through the suppressor to form a flowing sump for electrolyte ion as well as providing the water for the electrolysis generating acid or base for suppression. Thus, no external regenerant is required and the suppressor is continuously regenerated.

In PCT Publication WO 99/11351, published Mar. 11, 1999, and incorporated herein by reference, method and apparatus are disclosed for generating an acid or base eluent in an aqueous solution and for simultaneously suppressing conductivity of the eluent in an ion exchange bed after chromatographic separation in an ion chromatography system. In one disclosed embodiment, the suppressor and eluent generator comprises: a flow-through suppressor and eluent generator bed of ion exchange resin having exchangeable ions of one charge, positive or negative, having an inlet and an outlet section in fluid communication with fluid inlet and outlet conduits, respectively; an electrode chamber disposed adjacent to said suppressor and eluent generator bed inlet section and having fluid inlet and outlet ports; a flowing aqueous liquid source in fluid communication with said electrode chamber inlet port; a first electrode disposed in said electrode chamber; a barrier separating said suppressor and eluent generator bed from said electrode chamber, the barrier preventing significant liquid flow but permitting transport of ions only of the same charge as said suppressor and eluent generator bed resin exchangeable ions; and a second electrode in electrical communication with said resin bed outlet section. The suppressor and eluent generator is used with a flow-through separator bed of ion exchange resin having exchangeable ions of opposite charge to the exchangeable ions of said suppressor and eluent generator bed, said separator bed having a sample inlet port and an effluent outlet port, said electrode chamber outlet port being in fluid communication with said separator bed inlet port, said separator bed outlet being in fluid communication with said suppressor and eluent generator bed inlet port, and a detector downstream from the generator. The aqueous liquid source can be an independent reservoir or can be a recycle conduit from the detector.

For anion analysis, one method includes (a) flowing an aqueous liquid sample stream containing anions to be detected and cation hydroxide through a separator bed of anion exchange resin with exchangeable anions to form liquid effluent including separated anions and said cation hydroxide; (b) flowing said aqueous effluent from said separator bed through a flow-through suppressor and eluent generator bed comprising cation exchange resin including exchangeable hydronium ions, so that said cation hydroxide is converted to weakly ionized form, and some of said exchangeable hydronium ions are displaced by cations from said cation hydroxide, said suppressor and eluent generator bed having inlet and outlet sections and inlet and outlet ports, liquid effluent from said suppressor and eluent generator bed flowing through said outlet port; (c) flowing an aqueous liquid through a cathode chamber proximate to said suppressor and eluent generator bed inlet section and separated by a barrier therefrom, said barrier substantially preventing liquid flow between said cathode chamber and said suppressor and eluent generator bed inlet section while providing a cation transport bridge therebetween; (d) applying an electrical potential between a cathode in said cathode chamber and an anode in electrical communication with said suppressor and eluent generator bed outlet section, whereby water is electrolyzed at said anode to generate hydronium ions to cause cations on said cation exchange resin to electromigrate toward said barrier and to be transported across said barrier toward said cathode in said cathode chamber while water in said chamber is electrolyzed to generate hydroxide ions which combine with said transported cations to form cation hydroxide in said cathode chamber; (e) flowing said cation hydroxide from said cathode chamber to the inlet of said separator column; and flowing the effluent liquid from said suppressor and eluent generator bed past a detector in which said separated anions are detected. After passing the detector, the effluent liquid can be recycled to said cathode chamber. The system can be used for cation analysis by appropriate reversal of the cation and anion functional components.

In a second disclosed embodiment of a suppressor and eluent generator bed, the second electrode is not in direct contact with the suppressor and eluent generator bed. Instead, it is adjacent the suppressor and eluent generator bed outlet section in a second electrode chamber similar to the one described above. In this embodiment, aqueous liquid exiting the detector may be recycled to the inlet of the second electrode chamber.

In a third embodiment, similar to the second one, aqueous liquid from a reservoir is pumped to the inlet of the second electrode chamber. Liquid from the outlet of the second electrode chamber is directed to the inlet of the first electrode chamber. Liquid flowing out of the first electrode chamber is directed to the inlet of the separator bed.

Publication WO 99/11351 also discloses a method of anion analysis using two electrode chambers separated from the suppressor and eluent generator bed which includes the following steps: (a) flowing an aqueous liquid sample stream containing anions to be detected and a cation hydroxide through a separator bed of anion exchange resin with exchangeable anions to form a liquid effluent including separated anions and said cation hydroxide; (b) flowing said aqueous liquid effluent from said separator bed through a flow-through suppressor and eluent generator bed comprising cation exchange resin including exchangeable hydronium ions, so that said cation hydroxide is converted to weakly ionized form, and some of said exchangeable hydronium ions are displaced by cations from said cation hydroxide, said suppressor and eluent generator bed having inlet and outlet sections and inlet and outlet ports, liquid effluent from said suppressor and eluent generator bed flowing through said outlet port; (c) flowing an aqueous liquid through an anode chamber proximate to said suppressor and eluent generator bed outlet section and separated by a first barrier therefrom, said first barrier substantially preventing liquid flow between said anode chamber and said suppressor and eluent generator bed outlet section while providing a cation transport bridge therebetween, said aqueous liquid exiting said anode chamber as an anode chamber aqueous liquid effluent; (d) flowing an aqueous liquid through a cathode chamber proximate to said suppressor and eluent generator bed inlet section and separated by a second barrier therefrom, said second barrier substantially preventing liquid flow between said cathode chamber and said suppressor and eluent generator bed inlet section while providing a cation transport bridge therebetween; (e) applying an electrical potential between an anode in said anode chamber and a cathode in said cathode chamber, whereby water is electrolyzed at said anode to generate hydronium ions which are transported across said first barrier to cause cations on said cation exchange resin to electromigrate toward said second barrier and to be transported across said second barrier toward said cathode in said cathode chamber while water in said cathode chamber is electrolyzed to generate hydroxide ions which combine with said transported cations to form cation hydroxide in said cathode chamber; (f) flowing said cation hydroxide from said cathode chamber to the inlet of said separator bed; and (g) flowing the effluent from said suppressor and eluent generator bed past a detector in which said separated anions are detected.

The anode chamber aqueous liquid effluent may be recycled through said cathode chamber. Alternatively, after detection in step (g), the suppressor and eluent generator bed effluent may be recycled through said anode chamber.

In PCT Publication WO 99/44054, published Sep. 2, 1999, and incorporated herein by reference, method and apparatus are disclosed for continuously electrolytically suppressing the conductivity of an eluent in an ion exchange bed previously used in separating ions in a separator bed.

Referring first to the apparatus, the suppressor includes (a) a flow-through suppressor bed of ion exchange resin having exchangeable ions of one charge, positive or negative, having a liquid sample inlet and an outlet section in fluid communication with suppressor inlet and outlet ports, respectively, (b) a first electrode chamber disposed adjacent to said suppressor inlet section and having fluid inlet and outlet ports, (c) a first electrode disposed in said first electrode chamber, (d) a barrier separating said suppressor bed from said first electrode chamber, said barrier preventing significant liquid flow but permitting transport of ions only of the same charge as said suppressor bed resin exchangeable ions, (e) a second electrode in electrical communication with said resin bed outlet section, and (f) a recycle conduit providing fluid communication between said suppressor outlet port and said electrode chamber inlet port.

Opposite faces of the barrier are in electrical communication with the first and second electrodes, respectively, in direct contact or through conductive medium. For example, the second electrode is in electrical communication with the barrier through the conductive suppressor bed.

The suppressor is normally used in combination with (g) a flow-through separator bed of ion exchange resin having exchangeable ions of opposite charge to the exchangeable ions of said suppressor bed, said separator bed having a sample inlet port and an outlet port, said separator bed outlet port being in fluid communication with said suppressor bed inlet port, and with a detector disposed in the path of said recycle conduit to detect sample flowing through said conduit.

In one embodiment, the second electrode is disposed in contact with said ion exchange resin in said suppressor outlet section. In another embodiment, the suppressor combination includes (h) a second electrode chamber disposed adjacent to said suppressor outlet section and having fluid inlet and outlet ports, and (i) a second barrier separating said suppressor bed from said second electrode chamber, said barrier preventing significant liquid flow but permitting transport of ions only of the same charge as said suppressor bed resin exchangeable ions, said second electrode being disposed in said second electrode chamber.

For anion analysis, the suppressor bed ion exchange resin is a cation exchange resin, the first electrode is a cathode, and the second electrode is an anode. The opposite polarities apply for cation analysis.

Referring to one embodiment of the method, anion analysis is performed by the following steps: (a) flowing an aqueous liquid sample stream containing anions to be detected and cation hydroxide through a separator bed of anion exchange resin with exchangeable anions to form liquid effluent including separated sample anions and said cation hydroxide,(b)flowing said aqueous effluent from said separator bed through a flow-through suppressor and comprising cation exchange resin including exchangeable hydronium ions, so that said cation hydroxide is converted to weakly ionized form, and some of said exchangeable hydronium ions are displaced by cations from said cation hydroxide, said suppressor bed having inlet and outlet sections and inlet and outlet ports, liquid effluent from said suppressor bed flowing through said outlet port,(c) flowing the effluent liquid from said suppressor past a detector in which said separated sample anions are detected, (d) recycling said liquid effluent from said detector through a cathode chamber proximate to said suppressor bed inlet section and separated by a first barrier therefrom, said first barrier substantially preventing liquid flow between said cathode chamber and said suppressor bed inlet section while providing a cation transport bridge therebetween, and (e) applying an electrical potential between a cathode in said cathode chamber and an anode in electrical communication with said suppressor bed outlet section, whereby water is electrolyzed at said anode to generate hydronium ions to cause cations on said cation exchange resin to electromigrate toward said barrier and to be transported across said barrier toward said cathode in said cathode chamber while water in said cathode chamber is electrolyzed to generate hydroxide ions which combine with said transported cations to form cation hydroxide in said cathode chamber. In another embodiment, the liquid effluent is recycled through an anode chamber proximate to said suppressor bed outlet section and separated by a barrier of the same type as the first barrier. The anode is disposed in the anode chamber.

BRIEF DESCRIPTION OF THE DRAWINGS

FIGS. 1–4 are schematic representations of different combinations of eluent generators and suppressors according to the present invention.

FIGS. 5–11 are chromatograms of different experiments using the methods and apparatus of the present invention.

SUMMARY OF THE INVENTION

The apparatus of the present invention comprises (a) a chromatographic separator comprising chromatographic separating medium for separating ionic species of a sample eluted therethrough with an eluent solution comprising an electrolyte including electrolyte ions of opposite charge to said ionic species, said chromatographic separator having an inlet and an outlet, (b) a suppressor for treating effluent eluted from said chromatographic separator, said suppressor including (1) a chromatography effluent compartment having an inlet and an outlet, (2) an ion receiving compartment having an inlet and an outlet, (3) at least a first suppressor ion exchange barrier partitioning said chromatography eluent compartment and ion receiving compartment and defining therewith a chromatography effluent flow channel and an ion receiving flow channel, respectively, each having an inlet and an outlet, said first suppressor barrier being preferentially permeable to ions of one charge only, positive or negative, of the same charge as said transmembrane electrolyte ions, (c) a detector suitable for detecting separated ionic species having an inlet and an outlet, said detector inlet communicating with said chromatography effluent channel outlet to receive treated chromatography effluent therefrom, (f) an eluent generator comprising: (1) at least a first generator electrode chamber having an inlet and outlet, (2) a first generator electrode disposed in said first generator electrode chamber, (3) an electrolyte ion reservoir, (4) at least a first charged generator barrier separating said first eluent generator electrode chamber from said electrolyte ion reservoir, said first barrier preventing significant liquid flow but permitting transport of said transmembrane electrolyte ions, (5) a second generator electrode in electrical communication with said first electrode through said electrolyte ion reservoir, said second generator electrode being on the opposite side of said first generator barrier from said first generator electrode, (6) a first conduit providing fluid communication between said ion receiving compartment outlet and said second generator electrode, and (7) a source of aqueous liquid in fluid communication said first generator electrode chamber inlet, and (8) a second conduit providing fluid communication between said first generator electrode chamber outlet and said chromatographic separator inlet. Aqueous liquid is supplied to said ion receiving flow channel from an independent source or by recycle from the detector.

In another embodiment, eluent generator further comprises a second charged generator barrier of the same charge as said first barrier, said second generator barrier being disposed between said second electrode and said electrolyte ion reservoir, thereby forming a second generator electrode chamber, said second generator barrier preventing significant liquid flow but permitting transport of ions of the same charge as said electrolyte ions.

The apparatus may also include a second suppressor electrode chamber having an inlet and an outlet and a second electrode disposed in said second electrode chamber, said second suppressor electrode chamber inlet being in fluid communication with said detector effluent outlet, said first conduit providing fluid communication between said second suppressor electrode chamber outlet and said second generator electrode.

A method of analysis of ionic species according to the invention comprises: (a) eluting a sample containing ionic species to be detected in a water-containing eluent solution comprising electrolyte, including electrolyte ions of opposite charge to said ionic species, through a chromatographic separator, having an inlet and an outlet, and comprising chromatographic separation medium in which said ionic species are separated, (b) flowing the chromatography effluent from said chromatographic separator outlet through a chromatography effluent flow channel of a suppressor in which said chromatography effluent flow channel is separated by an at least a first suppressor ion exchange barrier with exchangeable ions, of the same charge as said electrolyte ions, from an ion receiving flow channel having an inlet and an outlet, (c) flowing the treated effluent from said chromatography effluent flow channel through a detector in which said separated ionic species are detected, (d) flowing an aqueous liquid through said ion receiving flow channel so that electrolyte ions from the chromatography effluent flowing through said chromatography effluent flow channel are diffused through said first suppressor barrier into said ion receiving flow channel, converting said electrolyte in said chromatography effluent flow channel to weakly dissociated form, (e) passing an electrical potential between said chromatography effluent flow channel and said ion receiving flow channel transverse to liquid flowing through said chromatography effluent flow channel to assist diffusion of said electrolyte ions through said first suppressor barrier substantially preventing liquid flow while providing an ion transport bridge for said electrolyte ions, said ion receiving flow channel being of opposite charge to said electrolyte ions, (f) directing the effluent from said ion receiving flow channel through an eluent generator including at least a first generator electrode in a first generator chamber separated from an electrolyte ion reservoir by a first generator barrier, said detector effluent flowing past a second generator electrode in said eluent generator, (g) flowing a water-containing stream to said first generator electrode chamber inlet, (h) applying an electrical potential between said first and second electrodes, whereby water adjacent said second electrode is electrolyzed to hydronium ions or hydroxide ions of the same charge as said electrolyte ions to assist the same to migrate toward said first generator barrier and to be transported across the same to a position adjacent said first generator electrode while water adjacent said first electrode in said first generator electrode chamber is electrolyzed to generate hydroxide or hydronium ions of opposite charge to said electrolyte ions to combine therewith to form an acid or base, and (i) flowing the acid or base generated in said first generator electrode chamber to said chromatographic separator inlet.

DETAILED DESCRIPTION OF PREFERRED EMBODIMENTS

The system of the present invention is useful for determining a large number of ionic species so long as the species to be determined are solely anions or solely cations. Suitable samples include surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

In general, the present invention relates to an ion chromatography apparatus and method using a combination of a continuous electrolytic suppressor and a separate eluent generator. Ion chromatography is performed in a conventional manner by chromatographic separation, suppression, and detection. In one embodiment, suppression is performed in a flow-through ion exchange suppressor with at least one external electrode as described in PCT Publications WO 99/11351 or WO 99/44054, incorporated herein by reference, and referred to as the "matrix suppressor." In another embodiment, the suppressor is of the self-regenerating type described in U.S. Pat. No. 5,248,426, incorporated herein by reference and is referred to herein as the "membrane suppressor." This invention relates to using suppressors of the foregoing general type in combination with an eluent generator which is remote from the suppressor but which serves to generate chromatography eluent from a recycled detector effluent stream after it passes through the detector effluent flow channel of the suppressor. The eluent produced in the eluent generator is recycled to the chromatography separation column for use as the eluent for chromatographic separation. The description will first refer in general terms to th e suppression portion of the invention.

Referring to the matrix suppressor embodiment, the chromatography effluent flows through the chromatography effluent flow channel of the suppressor separated by an ion exchange barrier, from the detector effluent flow channel suitably including a suppressor electrode. The treated effluent from the chromatography effluent flow channel flows through a detector and then is recycled through the detector effluent flow channel. The electrolyte ions are diffused through the suppressor ion exchange barrier into the detector effluent flow channel, converting the electrolyte to a weakly disassociated form. Electrical potential is passed between the chromatography effluent flow channel and the one detector effluent flow channel transverse to liquid flow to assist diffusion. One embodiment of this portion of the apparatus is described in WO 99/144054. The effluent from the detector effluent flow channel is passed to the eluent generator to be described below. The effluent produced in the eluent generator is then used as the eluent for chromatographic separation.

The purpose of the suppressor stage is to reduce the conductivity, and hence noise, of the analysis stream background while enhancing the conductivity of the analytes (i.e., increasing the signal/noise ratio), while maintaining chromatographic efficiency. The suppressor has electrodes in electrical contact with the resin, which permits continuous electrochemical regeneration. The electrodes are separated from the resin by a barrier which permits ion movement but is impermeable to liquid flow under typical operating pressures. The device may have several ion exchange connectors and electrodes in order to increase the flux of regenerant ions and eluent counter-ions. Electrochemical regeneration of the packed bed suppressor, by application of a direct current (DC) voltage, is continuous during the analysis by electrolytically splitting an aqueous liquid stream which is separated from the eluent flow by the ion exchange connectors. The electrolytically generated hydronium or hydroxide passes through the ion exchange connector and migrates through the ion exchange resin to neutralize the eluent. Eluent counter-ions pass through the ion exchange connector and are swept to waste by the aqueous liquid stream. In one embodiment, the aqueous liquid stream is the suppressed eluent. In another embodiment, the aqueous liquid stream is an independent water source, preferably deionized water.

The gases created by the electrolysis of the aqueous liquid stream, hydrogen and oxygen, are separated from the eluent flow by the ion exchange connector so that detection is not adversely affected by the gas production.

In this electrolytic packed bed suppressor form of the matrix suppressor embodiment, apparatus is provided to perform the above continuously regenerated packed bed suppressor methods. Such apparatus includes a suppressor with an ion exchange resin bed, liquid barriers that prevent liquid flow but permit ion transport and means for applying a continuous electrical potential to electrolyze water in a flowing stream and thus continuously regenerate suppressor ion exchange resin to suppress the electrolyte in the eluent stream.

In one embodiment, the present invention relates to the use of a continuous electric field during electrochemical suppression to minimize noise during detection of the ionic species. When used in this configuration, the requirement for chemical regenerant is eliminated. Also, the device can tolerate high system backpressure. Further, it has low noise since the electrolysis reaction occur in a chamber separate from the eluent flow and reduced manufacturing costs due to the simple design. As used herein, the term continuous electrolytically regenerated packed bed suppressor (CERPBS) will refer to the packed bed embodiment of the suppressor.

In the CERPBS, the electrodes are in electrical contact with the ion exchange resin either through an ion exchange connector in contact with the resin or the electrode is directly embedded in the resin. At least one of the electrodes is separated from the eluent flow path by the ion exchange connector, but still in electrical contact or communication with the resin. Also, the barrier is in electrical communication with both the suppressor bed resin and both electrodes. This configuration permits eluent counter-ions to be removed from the eluent stream and replaced with either hydroxide or hydronium to form water or other weakly conducting aqueous streams. For anion analysis using sodium hydroxide eluent, the suppressor contains cation exchange resin which is continually regenerated to the hydronium ion form by formation of hydronium ions at the anode, which migrate toward the cathode, displacing sodium ions from the ion exchange sites. At least the cathode is separated from the eluent stream by the ion exchange connector so that the sodium ions are removed from the eluent stream and exit the suppressor as sodium hydroxide. Current is maintained between the electrodes by movement of ions along ion exchange sites in the ion exchange material in the bed. It is also possible to have the anode separated from the eluent by an ion exchange connector. In this configuration, the electrolytically produced hydronium ion passes through the ion exchange connector and into the cation resin being driven towards the cathode under the force of the electric field. This configuration permits the continuous regeneration of the suppressor without the need to interrupt the analysis cycle to regenerate the suppressor.

One preferred form of matrix suppressor is a resin bed packed with ion exchange resin particles. However, other forms of matrices can be used, such as a porous continuous structure with sufficient porosity to permit flow of an aqueous stream at a sufficient rate for use in chromatography without undue pressure drop and with sufficient ion exchange capacity to form a conducting bridge of cations or anions between the electrodes. One form of structure is a porous matrix or a sponge-like material formed of sulfonated, cross-linked polystyrene with a porosity of about 10 to 15% permitting a flow rate of about 0.1 to 3 ml/min. without excessive pressure drop.

The details of the present invention will first be described with respect to the above matrix form of suppressor in combination with one embodiment of the eluent generator. Briefly described, in that embodiment the effluent from the detector effluent flow channel of the matrix suppressor, containing acid or base, is directed to an eluent generator including a first generator electrode chamber and a first generator electrode disposed in that chamber. The generator also includes a charged barrier separating the electrode chamber from an electrolyte ion reservoir. The barrier prevents significant liquid flow but permits transport of electrolyte ions. In one form of electrolyte reservoir, a matrix of the same type described above with respect to the suppressor column may be employed, specifically a packed bed of ion exchange resin or a porous matrix.

A second generator electrode of opposite charge to the first one is disposed in electrical communication with the first one through the electrolyte ion reservoir on the opposite side of the first generator barrier from the first generator electrode. A conduit connects the outlet of the detector effluent compartment and the second generator electrode. Aqueous liquid flows through the first generator electrode chamber to contact the first generator electrode. In one embodiment, such liquid is the outlet stream from the electrolyte ion reservoir. Electrolyte ions pass from the electrolyte ion reservoir through the charged generator barrier into the first eluent generator electrode chamber under the influence of the electrode being maintained of opposite charge to the electrolyte ion. In the first electrolyte ion chamber, an acid or bases generated under the same electrochemical reactions described above with respect to the suppressor.

Referring to FIG. 1, an ion chromatography system is illustrated using a CERPBS form of suppressor and one embodiment of the eluent generator. The system includes an analytical pump, not shown, connected by tubing 12 to sample injection valve 14 which in turn is connected by tubing 16 to a flow-through chromatographic separator 18 typically in the form of a chromatographic column packed with chromatographic resin particles. The effluent from chromatographic column 18 flows through tubing 20 to a packed ion exchange resin bed flow-through suppressor 22. Typically, suppressor 22 is formed of a column 24 packed with an ion exchange resin bed 26 of the type used for ion chromatography suppression. Electrodes, in a form to be described below, are spaced apart in the suppressor, with at least one electrode separated from the resin by a barrier described below. The electrodes are connected to a direct current power supply, not shown. The configuration is such that with an aqueous stream flowing through the suppressor and the application of power, water in the aqueous stream is electrolyzed to form a source of hydronium ion or hydroxide ion to continuously regenerate the ion exchange resin bed during the analysis.

The suppressor effluent is directed through tubing 30 to a suitable detector 32 and then eventually to waste. A preferred detector is a conductivity detector with a flow-through conductivity cell. The chromatography effluent flows through the cell.

Suppressor 22 generates hydronium ions (and oxygen gas) at the anode and hydroxide ions (and hydrogen gas) at the cathode. If the power supply were turned off, the system would operate in the manner of a standard ion chromatography system with a packed bed suppressor. That is, a water-containing eluent solution including electrolyte is directed from the pump and through tubing 12. Sample is injected through sample injection valve 14, and is directed by tubing 16 into chromatographic column 18 to form a first chromatography effluent including separated ionic species of the sample. For simplicity of description, unless otherwise specified the system will be described with respect to the analysis of anions using an eluent solution including sodium hydroxide as the electrolyte.

A suitable sample is supplied through sample injection valve 14 which is carried in a solution of eluent supplied from pump 10. Anode 36 is disposed at the outlet end of resin bed 26 in intimate contact with the resin therein. The effluent from bed 26 is directed to a detector suitably in the form of a flow-through conductivity cell 32 of the conductivity detector (not shown), for detecting the resolved anions in the effluent, connected to a conductivity meter.

In the detector, the presence of anions produces an electrical signal proportional to the amount of ionic material. Such signal is typically directed from the cell to a conductivity meter, thus permitting the detection of separated ionic species of interest (anions for anion analysis).

In a preferred embodiment, detection is by electrical conductivity and so the present system is described using ion conductivity detector. However, other forms of detectors may be used including UV-visible absorbance, fluorescence, mass spectrometry, and inductive coupled plasma spectrometry detectors. Detection of the present invention will be described with respect to a conductivity detector.

The system also includes means for pressurizing the effluent from suppressor 22 prior to detection to minimize adverse effect of gases (hydrogen or oxygen) generated in the system as will be described hereinafter. As illustrated in FIG. 1, such pressurizing means comprises a flow restrictor 38 downstream of conductivity cell 32 to maintain the ion chromatography system under pressure.

Column 24 is typically formed of plastic conventionally used for an ion exchange column. It has a cylindrical cavity of a suitable length, e.g., 60 mm long and 4 mm in diameter. It is packed with a high capacity cation exchange resin, e.g., of the sulfonated polystyrene type. The resin is suitably contained in the column by a porous frit which serves to provide an outlet to the column. In the illustrated embodiment, the porous frit is porous electrode 36 which serves the dual function of containment of the resin and as an electrode.

A barrier 40 separates bed 26 from electrode 42 in the interior of a hollow housing defining an ion receiving flow channel in electrode chamber 44 preventing any significant liquid flow but permitting transport of ions only of the same charge as the charge of exchangeable ions on resin bed 26. For anion analysis, barrier 40 is suitably in the form of a cation exchange membrane or plug separating electrode chamber 44 from the cation exchange resin.

Electrode 42 in electrode chamber 44 also suitably is in the form of an inert metal (e.g., platinum) porous electrode in intimate contact with barrier 40. An electrode is fabricated in a way to permit good irrigation of the electrode/membrane interface when water is passed through electrode chamber 44. The electrode is suitably prepared by crumpling and forming a length of fine platinum wire so as to produce a roughly disc-shaped object that allows easy liquid flow-throughout its structure and at the electrode membrane interface. Good contact between the disc-electrode 42 and barrier 40 is maintained simply by arranging that the one press against the other. The electrode can extend across all or part of the aqueous liquid flow path through electrode chamber 42 to provided intimate contact with the flowing aqueous stream.

A conduit 48 is provided to direct the aqueous liquid stream to the inlet 50 of electrode chamber 44. Conduit 52 takes the effluent from chamber 44 to the eluent generator. All conduits may be made from narrow bore plastic tubing. However, if desired, parts of conduits 30 and 48 may be made out of stainless steel tubing. When the metal conduit is allowed to touch the platinum electrodes, it makes electrical contact with the electrodes as well as being conduits for fluid flow. This provides a means of making electrical contact with the electrodes that is at the same time easy to seal against liquid leakage.

The line X—X is illustrated across the resin bed 26. For reasons which will be explained below, the resin upstream of the dotted line is predominantly or completely in the form of the cation counter ion of the base used as the electrolyte during separation. Downstream of the line X—X, the resin is predominantly or completely in the hydronium form. The line X—X represents the interface. As used herein, the terms "anion or cation or ion exchange beds" refer to flow-through beds of anion or cation exchange material through which the aqueous liquid stream flows. Unless otherwise stated, the term "cation" excludes hydronium ions and the term "anion" excludes hydroxide ions. Because of its ready availability and known characteristics, a preferred form of ion exchange bed is a packed ion exchange bed of resin particles. It is desirable that the resin particles be tightly packed in the bed, to form a continuous ion bridge or pathway for the flow of ions between electrodes 36 and 42. Also, there must be sufficient spacing for the aqueous stream to flow-through the bed without undue pressure drops.

As defined herein, the portion of bed 26 upstream of the line X—X is referred to as the suppressor bed inlet section 26a. Conversely, the portion of the bed downstream of the line X—X is referred to as the suppressor bed outlet section 26b. As illustrated, barrier 40 of electrode chamber 44 is disposed adjacent bed inlet section 26a and, therefore, primarily is in the cation form.

The principle of operation of the system for anion analysis is as follows. An aqueous liquid stream containing anions to be detected and a cation (e.g., potassium) hydroxide flows through separator bed 18 of anion exchange resin with exchangeable anions to form a liquid effluent including separated anions and the cation hydroxide. Anion exchange resin in bed 18 is of a suitable conventional low capacity form used for ion chromatography as illustrated in U.S. Pat. Nos. 3,897,213, 3,920,397, 3,925,019 and 3,926,559. For example, bed 18 has typically a total capacity of about 0.01 to 0.1 milliequivalents. As is conventional, the anion exchange capacity of the separator is low in comparison to that of the suppressor.

The ratio of the ion exchange capacities of the ion exchange resin in suppressor bed 26 to separator bed 18 may be the same as used for ion chromatography using a conventional packed bed suppressor, e.g. from 10:1 to 1000:1.

For anion analysis, a polarizing DC potential is applied between cathode 42 and anode 36, and the following reactions take place.

The water is electrolyzed and hydronium ions are generated at anode 36 according to the following reaction:

$$H_2O - 2e \rightarrow 2H^+ + \tfrac{1}{2}O_2\uparrow. \qquad (1)$$

This causes cations in the cation exchange resin bed 26 to migrate to barrier 40. This, in turn, displaces hydronium ions upwardly through bed 26 which causes a similar displacement of cations ahead of them. The cations electromigrate toward the barrier 40 to be transported across the barrier 40 toward cathode 42 in cathode chamber 44 while water is electrolyzed at cathode 42 to generate hydroxide ions according to the following reaction:

$$2H_2O + 2e \rightarrow 2OH^- + H_2\uparrow. \qquad (2)$$

The cations which have transported across the barrier combine with the generated hydroxide ions to form cation hydroxide in cathode chamber 44. The effluent from separator bed percolates through the cation form resin in inlet bed section 26 until it reaches the hydronium form resin in bed section 26 where it is neutralized while the cation is retained on the resin. At this point, the anion salts are converted to their respective acids and the cation hydroxide is converted to weakly ionized form, water.

The suppressed effluent liquid containing the separated anions leaves bed 26 through the conduit 30 and passes to conductivity cell 32 in which the conductivity of the separated anions is detected.

The effluent from conductivity cell 32 passes through flow restrictor 38 and conduit 48 and is recycled to electrode chamber 44. This provide s a source of aqueous liquid to permit continuous reaction in electrode chamber 44 by passing the formed acid or base to waste in a continuous stream.

The net result of the electrode reactions and the electromigration of the resin counterions are: the production of cation (e.g., potassium) hydroxide in the region of the cathode, and electrolytic gases at the two electrodes. Specifically, the electrode reactions produce, hydrogen and oxygen which are carried out of the suppressor into the chromatography system.

When the hydronium ion/cation boundary line X—X is reached, the cation (shown as potassium) hydroxide is neutralized as a conventional suppression according to the following equation:

$$KOH + H^+R^- \rightarrow K^+R^- + H_2O, \qquad (3)$$

wherein R is the cation exchange resin. The $K^+R^-$ indicates that the ion exchange resin retains the cation as its exchangeable ion.

The flux of hydronium in the resin phase toward bed inlet section 26a is equivalent to or greater than the flux of cation hydroxide in the mobile phase toward bed outlet section 26b. Since the balance prevails at different current levels, the position of th e hydronium/cation boundary line X—X remains fixed. Thus, the system operates as a continuous suppressor of cation hydroxide.

The suppressor of FIG. 1 has been described with respect to a system for the analysis of anions. However, the system is also applicable to the analysis of cations. In this instance, electrode 36 is a cathode and electrode 42 is an anode. The ion exchange type of resin is reversed. Thus, the resin in separator bed 18 is a cation exchange resin and the resin in suppressor bed 26 is an anion exchange resin. The plug or membrane 40 is made of an anion exchange material.

Briefly described, the suppressor works as follows for the cation analysis. The aqueous liquid stream containing cations to be detected and an acid electrolyte aqueous eluent are directed through separator bed 18 including cation exchange resin. The effluent from separator bed 18 flows through suppressor bed 26 including anion exchange resin with exchangeable hydroxide ions. The acid in the eluent is converted to weakly ionized form. Some of the exchangeable hydroxide is displaced by anions from the acid.

An electrical potential is applied between the cathode 36 and anode 42. Water is electrolyzed at electrode 36 to generate hydroxide to cause anions on the anion exchange resin bed to electromigrate toward barrier 40 to be transported across the barrier toward the positively charged anode 42 in the ion receiving flow channel in electrode chamber 44 while water in chamber 44 is electrolyzed to generate hydronium ions which combine with the transported anions to form acid in the electrode chamber 44. The effluent liquid from the suppressor bed 26 flows past detector 32 in which separated cations are detected and is recycled to electrode chamber 44.

In another embodiment, not shown, a separate source of aqueous liquid is provided for the inlet of electrode chamber 42 instead of recycling the effluent from detector 32. Th is enables the use of a liquid containing an organic solvent or other component for separation in column 18 which could be detrimental if recycled to the eluent generator.

The exchangeable cations or anions for suppressor bed 26 and, thus for the acid or base electrolyte in the aqueous eluent, must also be sufficiently water soluble in base or acid form to be used at the desired concentrations. Suitable cations are metals, preferably alkali metals such as sodium, potassium, lithium and cesium. Known packing for high capacity ion exchange resin beds are suitable for this purpose. Typically, the resin support particles may be in the potassium or sodium form. Potassium is a particularly effective exchangeable cation because of its high conductance. Suitable other cations are tetramethyl ammonium and tetraethyl ammonium. Analogously, suitable exchangeable anions for cation analysis include chloride, sulfate and methane sulfonate. Typically, resin support particles for these exchangeable anions include Dowex 1 and Dowex 2.

Referring again to FIG. 1, one embodiment of the eluent generator is illustrated, describing first the system for anion analysis in which a base generated in electrode chamber 44 is directed to the eluent generator. This embodiment is analogous in electrochemical operation to suppressor 24. In this embodiment of the eluent generator, a suitable housing 54 contains an electrolyte ion reservoir in the form of a packed bed of ion exchange resin 56. Resin bed 56 is separated from a first generator electrode chamber 58 by a charged generator barrier 60 which prevents significant liquid flow but permits transport of electrolyte ions and thus may be of the type described with respect to suppressor barrier 40. A generator electrode 62 is disposed and enclosed in generator electrode chamber 58 and may be of the same type of construction as electrode chamber 44. At the opposite side of barrier 60 from electrode 62 is flow-through generator electrode 64 analogous in function and structure to suppressor electrode 36.

The electrochemical reactions described above with respect to the suppressor occur in the eluent generator and so are incorporated herein by reference. Thus, for analysis of anions, the line x—x separates the inlet section 56a from the outlet section 56b of resin bed 56. The feed stream in line 52 flows into inlet section 56a in the cation form while the outlet section is in the hydronium ion form. However, one difference is that the feed stream in conduit 52 already includes base. The feed stream exits packed resin bed 56 adjacent barrier 60 and flows across bed 56 and out the outlet through electrode 64 or past some other form of electrode as described above. Similarly, the packed bed includes resin in the electrolyte ion form (e.g., potassium or sodium) at its inlet end adjacent barrier 60 and in hydrogen ion form near the outlet end adjacent electrode 64.

In the illustrated embodiment of resin bed 56, the feed stream flows into bed 56 at the bottom or horizontally across the bed and then out of the bed. In another embodiment, the bed may be disposed vertically with flow either upwardly or downwardly through the column. One advantage of upward flow is that gas bubbles generated in the suppressor can be diffused through the bed.

In the method and apparatus disclosed in PCT Publication WO 99/11351, the eluent generator bed and the suppressor bed are in direct contact with each other and contained in a single flow-through module. In the present invention, the eluent generator and recycle module are isolated but in fluid communication with the suppressor module, the eluent generation and recycle functions are performed in one module, and the eluent suppression function is performed in a separate module. The present invention offers several advantages over the previous invention disclosed in PCT Publication WO 99/11351. First, a relatively large eluent generation and recycle module can be more readily combined to provide a relatively large reserve of $K^+$ ions for eluent generation and recycle. Second, the large device geometry offers the advantages of relatively low device resistance and the ability to generate relatively high concentration of acid or base eluent without excessive heat generation. Third, suppressor modules of different designs can be used in the present invention to provide optimal performance.

The same type of packed bed resin or other form of matrix may be used in the eluent generator as in the suppressor. As illustrated, the source of aqueous liquid flowing through generator electrode chamber 58 can be liquid recycled from the outlet of the resin bed. Specifically, such liquid flows through conduit 65, and preferably includes a means of deionizing the exit stream such as a mixed (cation and anion exchange) bed water polishing column 67. The water polisher column is typically 2 to 40 cm in length and 0.5 to 10 cm in internal diameter. From there, the stream flows through conduit 69 and flows to chamber 58. In the case of anion analysis, the cation hydroxide is generated in chamber 58 adjacent the cathode in the manner described above with respect to the suppressor. The water source after passing through the water polisher is deionized and so does not interfere the analysis. From chamber 62, the liquid flows through conduit 64 and optionally through a degasing tube 56 and conduit 12 through the injector 14 as set forth above. The degaser 56 may be of the type used in Dionex EG40 eluent generator (Dionex Corporation, Sunnyvale, Calif., U.S.A.).

In another embodiment, not shown, the liquid effluent from the eluent generator 54 flows to waste and an independent aqueous liquid source (e.g., deionized water) is passed through generator electrode chamber 58.

Although the electrochemical operation of the eluent generator 54 is analogous to that of the suppressor 24, typically there are differences in their geometry and operating conditions. The electrolyte ion reservoir (ion exchange bed 56) in the eluent generator 54 normally has a significantly larger volume than the ion exchange bed 26 in the suppressor 24. Suitably, ion exchange bed 56 can have a volume of at least 1 mL to 2 mL to as high as 1000 mL or higher. Typical dimensions of the reservoir in the eluent generator can be about 10 to 100 mm in diameter and 20 to 150 mm in length. In contrast, a typical suppressor has a volume of no greater than about 1.0 mL and typically from about 0.03 to 2.0 mL. The ion exchange bed 26 in the suppressor 24 is typically 2 to 6 mm in diameter and 10 to 80 mm in length. Suitably, the volume ratio of the electrolyte ion reservoir to the suppressor is at least 10:1, to as high as 10,000:1 or more.

The DC current applied to the eluent generator is typically in the range of 0.1 to 250 mA. DC current of 250 mA or higher may be used to generate a higher concentration of acid or base eluents at a given flow rate. The flow rate through the electrode chamber 58 is typically in the range of 0.1 to 3.0 mL/min. When operating the apparatus shown in FIG. 1, the DC current applied to the suppressor 24 should be higher than that applied to the generator 54 and is typically in the range of 1 to 500 mA. Higher applied current may be used to suppress a higher concentration of eluents. The device operating voltage for the eluent generator and the suppressor is typically in the range of 5 to 100 V.

In one embodiment set forth above, the ion exchange medium, typically ion exchange resin bed 56, is packed with the same type of high capacity ion exchange resin as is used in column 25 set forth above. In another embodiment, termed a "dual bed", the ion exchange medium includes an upstream portion and an adjacent downstream portion of different ion exchange characteristics. For purposes of this description, the ion exchange medium will be described with respect to an ion exchange resin bed. In one preferred embodiment, the upstream ion exchange bed portion comprises a weakly acidic or weakly basic ion exchange resin layer of the same charge as the electrolyte ions, but not in the hydronium or hydroxide form. For example, for anion analysis and thus suppression of a basic electrolyte, the ion exchange material can be in the same form as the electrolyte to be suppressed, such as in $K^-$ or $Na^-$ form. In contrast, the downstream portion of the ion exchange bed comprises a downstream layer of strongly acid or strongly basic ion exchange material in hydronium ion or hydroxide ion form of the same charge as the electrolyte ions. Thus, for anion analysis, the downstream layer is in strongly acidic form of the type described above. A preferred weakly acidic cation exchange resin is a carboxylated resin in $K^+$ or $Na^-$ form. A preferred strongly acidic cation exchange resin layer is a sulfonated resin in hydronium ion form.

Conversely, for the generation of acid, the upstream bed layer typically is of a weakly basic ion exchange form (e.g., a resin with tertiary or a secondary amine function groups in methanesulfonate form or sulfate form) and the downstream bed layer is of the strongly basic ion exchange type (e.g., a resin with quaternary amine functional groups in hydroxide form).

For either type of weakly acidic or weakly basic upstream portion, the capacity preferably may be in the range of from about 0.4 to about 2.4 meq/mL. However, ion exchange materials of either higher or lower capacity may be also used. For the strongly acidic upstream bed portion, a suitable strongly acidic cation exchange resin is Dowex 50 WX8 in hydronium ion form and the weakly acidic cation exchange resin in the upstream layer suitably is a Bio-Rad Chelex-100 resin in potassium ion form.

An advantage of this dual-bed system is that the upward movement of the hydronium ions is impeded when the hydronium ion encounter the zone of weakly acidic resin because of the formation of weak acids. Thus, substantially all of the cations, (e.g., $K^+$ ions) are recycled minimizing the direct migration of hydronium ions to the cathode of the device. This leads to very high theoretical current efficiency.

The relative volume of the resin in the upstream bed portion and downstream bed portion can be varied significantly. For example, for some systems, the volumetric ratio of the upstream weakly acidic or basic resin to the downstream bed portion typically is on the order of about 1:10 to 1:5.

In a more preferred embodiment, the upstream ion exchange medium portion comprises an intermediate ion exchange medium layer between the upstream weakly acidic or basic ion exchange resin layer and the strongly acidic or basic downstream layer. In this instance, the intermediate layer comprises a strongly acidic or strongly basic ion exchange material of the same charge as the electrolyte ions, but not in hydronium or hydroxide ion form. Thus, for anion analysis, the intermediate layer is suitably in the form of the ion to be suppressed such as potassium ion, while for the cation analysis, the exchangeable ion is suitably in the methanesulfonate or sulfate form. The ionic strength of the strongly acidic or strongly basic ion exchange material in the intermediate layer is suitably of the same strength of that of the strongly acidic or strongly basic ion exchange resin in the downstream bed portion, the difference being that the exchangeable ions are in the cation or anion form rather than in the hydronium ion or hydroxide ion form. As used herein, the term "cation" excludes the hydronium ion and the term It is preferable that the intermediate layer be disposed above the X—X line described above. The zone of strongly acidic resin in the cation form serves the function of a "buffer" zone to further impede the flow of hydronium ion towards the cathode in anion analysis and to avoid intermediate formation of a weak acid zone with its consequent high electrical resistance as the result of the upward movement of hydronium ions when DC current is first applied to the device. The zone of weakly acidic cation exchange resin in potassium form and the zone of strongly acidic resin in the potassium ion form are preferably located above the X—X line, while the zone of strongly acidic resin in the hydronium ion form is preferably located below the X—X line for reasons discussed above.

The depth of the three layers can be varied to a significant extent. The strongly acidic cation exchange resin in the hydronium form (Zone A) preferably is the deepest layer, followed by the weakly acidic cation exchange resin in the potassium form (Zone B) a nd then by the intermediate buffer layer (Zone C). A typical ratio of the depth of Zone A to Zone B to Zone C is about 10:2:1.

Referring to FIG. 2, another embodiment of the invention using the single eluent generator as FIG. 1 is illustrated but using a suppressor with two electrode chambers as described with respect to FIG. 2 in WO 99/44054, incorporated herein by reference.

Like the embodiment in FIG. 1, the FIG. 2 suppressor embodiment may be us ed with a conventional packed ion exchange resin bed separator column. The principal difference between the suppressor embodiments of FIGS. 1 and 2 is that in the latter one, there are two external electrode chambers rather than one so that the analyte ions are prevented from contacting any electrodes. Like parts will be designated with like numbers for FIGS. 1 and 2.

In FIG. 2, the effluent from the separator column 18 flows in conduit 20 through suppressor 70 which includes a housing (suitably of cylindrical cross-section) including a body defining a central bore, screw threaded end caps, at opposite ends of the bore. Suppressor 70 contains a high-capacity ion exchange resin bed 72 of the type described above. Electrode chamber 74 contains electrode 76 separated from bed 72 by barrier 78, all of the same type described above. The difference from the suppressor of FIG. 1 is that the suppressor of FIG. 2 includes an electrode chamber 80 containing a second electrode 82 separated by barrier 84 from bed 72. Both electrode chambers 74 and 80 may be of the same type with the exception that the electrodes are of opposite polarity. Electrode 82 in electrode chamber 80 replaces electrode 36 in FIG. 1 which was in direct contact with the resin bed of the suppressor. The electrodes are connected to a DC power supply, not shown, and are suitably formed of platinum. As is conventional, the end caps include screw-threaded ports for connecting to the inlet and outlet tubing.

The effluent from suppressor 70 flows through line 86 and through detector 88 and line 90 to electrode chamber 80. The effluent from electrode chamber 80 is further recycled through line 92 to the inlet side of electrode chamber 74. The effluent from electrode chamber 70 passes through line 94 to the eluent generator which operates as described in FIG. 1.

In the suppressor of FIG. 2, resin bed 72, electrodes 76 and 82, and barriers 78 and 84 are in electrical communication. However, barriers 78 and 84 separate the sample eluent flow-through the suppressor 70 from the liquid flow in the anode and cathode chambers. The same reactions as in FIG. 1 occur at the anode and cathode. Specifically, for anion analysis, the foregoing description applies to the reaction in cathode chamber 70. Similarly, the same reaction occurs at anode 78 as described in FIG. 1 with respect to anode 36. However, the presence of barrier 84 creates the following difference in operation. The hydronium ions generated at anode 82 electrophoretically pass through barrier 84 to the cation exchange resin in bed 72 where they are driven in the resin toward cathode 72 in the manner described above. Similarly, cations from the eluent are displaced from the cation exchange resin by the flux of hydronium ions which combine with the eluent hydroxide to form water. This reaction scheme is as also set forth above. Similarly, the cations are electrophoretically driven through barrier 78 to electrode 76 where they associate with the hydroxide ions to form a base for passage to the eluent generator. The oxygen produced at the anode compartment and the hydroxide produced in the cathode department are swept away with the sodium hydroxide. Thus, no flow restrictor is necessary to minimize the effect of such gases on analysis since the gases are separated from the analytical system.

Another advantage of separating the anode and cathode by barriers 78 and 84 is that the eluent stream flowing through bed 72 does not pass over the electro-active surface of the electrodes where a solvent or analyte could be electrochemically modified. This can be important when an organic modifier is used in the eluent. For example, methanol, a common organic modifier with sodium hydroxide eluents, can be oxidized at the anode to formic acid which raises the background conductivity. With the electrode separated from the eluent compartment by the barriers, the eluent stream is not exposed to undesirable electrochemical reactions.

Referring to FIG. 3, another embodiment of the invention is illustrated using the eluent generator of FIGS. 1 and 2 in combination with a suppressor of the self-regenerating type described in U.S. Pat. No. 5,248,426, incorporated herein by reference. Referring to FIG. 3, the membrane suppressor embodiment is illustrated in which effluent from chromatography separator 18 passes through line 20 to the chromatography effluent compartment 100 of sandwich membrane suppressor 102. In this instance, the chromatography effluent compartment is sandwiched between two detector effluent compartments 104 and 106 and separated therefrom by ion exchange barriers 108 and 110, respectively. The structure of the membrane suppressor embodiment may be of the type disclosed in the aforementioned U.S. Pat. No. 5,352,360. As disclosed therein, ion conducting material such as inert metal screens may be placed in any of the compartments 100, 104 or 106 to improve the current efficiency of the devices. An electrical potential is applied across the sandwich suppressor 102, suitably by flat plate electrodes 112 and 114 disposed at the outside of the detector effluent compartments 104 and 106 as described in the above patent.

The suppressor effluent flows through line 116 to conductivity detector cell 118 for recycle in line 120 back to detector effluent compartments 104 and 106 serving as the flowing aqueous stream for the generation of an acid or base and for the suppression of the eluent in the chromatography effluent flowing into the suppressor in line 120. The details of operation of the suppressor to accomplish these objectives are described in detail in U.S. Pat. No. 5,350,360, incorporated at this point by reference. The effluent from suppressor 102 containing acid or base flows through line 122 to eluent generator 54 of the type described above in FIGS. 1 and 2.

Referring to FIG. 4, another embodiment of the invention is illustrated in which the suppressor of FIG. 3 is used in combination with a different form of eluent generator. Like parts of the combination outside of the eluent generator will be designated with like parts as in FIG. 3.

The principal difference between the eluent generator of FIGS. 3 and 4 is that electrode 64 of FIG. 3 is isolated from the electrolyte reservoir by a second barrier facilitating the use of an electrolyte reservoir in the form of an aqueous solution as well as a solid matrix, e.g., in the form of a packed ion exchange resin bed or other in exchange materials such as monoliths or foams as described above.

Referring specifically to FIG. 4, the acid or base effluent in line 122 is directed to generator chamber 124 of eluent generator 126. Electrode 128 is disposed in chamber 124 and is separated from electrolyte reservoir 130 by a generator barrier 132 which prevents significant liquid flow but permits transport of electrolyte ions.

Generator chamber 134 is disposed on the opposite of electrolyte reservoir 130 from generator 124. A second electrode 136 is contained within chamber 134 and is separated from electrolyte reservoir 130 by a barrier 138, suitably of the same type as barrier 132. Electrode chambers 124 and 134 and their component parts are suitably of the type described above with respect to generator electrode chamber 58. Also as described above, electrodes 128 and 136 are of opposite polarities. Similar electrochemical reactions occur at the anodes and cathodes as described for the embodiment of the eluent generator of FIG. 1. However, electrode 128 is isolated from electrolyte reservoir 130. In that regard, the eluent generator of FIG. 4 is similar to suppressors 70 of FIG. 2 in that both electrodes are isolated. One advantage of isolating both electrodes is that it facilitates the containment of an electrolyte reservoir in the form of an aqueous liquid. Alternatively, if desired, a solid form of electrolyte reservoir may be contained in the reservoir such as the matrix (e.g., packed ion exchange resin bed) described above, or the electrolyte reservoir may contain a mixture of liquid electrolyte solution and solid ion exchange materials.

The remainder of the eluent generator and its flow connections to the separator 18 are the same as that described above with respect to FIG. 1. Accordingly, that description is incorporated at this point by reference and like parts will be designated with like numbers.

The proper operating current for the suppressor depends on the eluent composition. For the anion analysis, the electrochemically generated hydronium flux must be greater than or equal to the incoming sodium hydroxide flux. This assures that every mole of hydroxide is neutralized by a mole of hydronium and that the sodium is displaced by hydronium through the ion exchange connector, to the cathode compartment which is swept to waste. Typically, the current is 110–160% of the eluent flux.

The operating voltage depends on the suppressor device geometry, electrode size, electrode spacing as well as the resin and ion exchange connector conductivity. The device is designed to minimize the voltage drop and typical operating voltages range from 10 to 100 volts. It is generally desirable to operate the device in the constant current mode since current can be directly related to the eluent concentration, and hence the regenerant flux required.

The suppressor includes means for applying an electrical potential through the ion exchange connectors and across the ion exchange resin. Any number of configurations may be employed so long as the potential is applied to a significant part of the resin for efficient regeneration and the eluent cations are removed through the ion exchange connector. In that regard, the anode and cathode should be spaced apart with the majority of the ion exchange resin disposed therebetween.

The following examples illustrate different aspects of the present invention.

EXAMPLE 1

This example illustrates the use of a continuous electrolytically regenerated packed bed suppressor and an eluent generator of the type illustrated in FIG. 1 for separation of common anions. As shown in FIG. 1, a DX500 ion chromatographic system (Dionex Corporation, Sunnyvale, Calif.) consisting of GP40 pump, an injection valve and an AS 11 separator column (4-mm ID×250-length) was used. A continuous electrolytically regenerated packed bed suppressor 22, as described in this disclosure, was used. The body of suppressor 22 consisted of a column (4-mm ID×70-mm length) packed with 200–400 mesh Dowex 50WX8 sulfonated ion exchange resin in hydronium form. The outlet of the suppressor bed was fitted with a porous Pt disk which was used to retain the ion exchange resin in the suppressor and serve as the device anode. A cation exchange membrane AMI-7000 (Membrane International, Glen Rock, N.J.) was used as the barrier 40 in the cathode chamber 44. A Model E3612A DC power supply (Hewlett Packard, Palo Alto, Calif.) was used to apply DC voltage to the anode 36 and the cathode 42 of the suppressor. A Dionex ED40 conductivity detector equipped with a flow-through conductivity cell was used to monitor the effluent from the suppressor. A piece of PEEK tubing (1/16-inch OD×0.003-inch ID×15 cm length) was used as the restrictor 38 to provide backpressure to the conductivity cell. The eluent generator was constructed using an EGC-KOH generator cartridge (P/N 53986, Dionex Corporation, Sunnyvale, Calif.). The parts of the EGC-KOH generator cartridge were used as the cathode chamber 58, cathode 62 and the barrier 60. The EGC-KOH cartridge was fitted with an anode chamber (1-inch ID×2.5-inch length) made of polypropylene. The anode chamber 54 was fitted with a perforated platinum electrode as the anode 64 at its outlet. The ion exchange resin bed 56 in the anode chamber 54 consisted of three sections including a bed (1-inch ED×0.3 inch length) of 200–400 mesh Chelex-100 resin in potassium form, and a bed (1-inch ID×0.2 inch length) of 200–400 Dowex 50WX8 resin in potassium form, and a bed (1-inch ID×2 inch length) of 200–400 Dowex 50WX8 resin in potassium form, and a bed (1-inch ID×2 inch length) of Dowex 50WX8 resin in hydronium form. The bed of 200–400 mesh Chelex-100 resin in potassium form was in direct contact with the barrier 60. The bed of 200–400 mesh Dowex 50WX8 resin was in direct contact with the platinum anode 64 at the chamber outlet. The bed of Dowex 50WX8 resin in the potassium form was sandwiched between the bed of Chelex-100 resin in potassium form and the bed of Dowex 50WX8 resin in hydronium form. Chelex-100 resin, a weakly acidic cation exchange resin, was used to stop the migration of hydronium ions from the anode to the cathode of the eluent generator in order to maintain the current efficiency of the device. A Dionex PeakNet 5.0 computer workstation was used for instrument control, data collection and processing.

FIG. 5 shows the separation of fluoride, chloride, nitrate, carbonate and sulfate on the AS11 column using the apparatus illustrated in FIG. 1. In this separation, the eluent generator was used to generate 10 mN KOH at 1.0 mL/min. The current applied to the suppressor was 50 mA and the operating voltage of the device was 50 V.

EXAMPLE 2

This example illustrates the use of a continuous electrolytically regenerated packed bed suppressor and an eluent generator of the type illustrated in FIG. 2 for separation of common anions. As shown in FIG. 2, a DX500 ion chromatographic system (Dionex Corporation, Sunnyvale, Calif.) consisting of a GP40 pump 10, an injection valve 14 and an AS15 separator column) 4-mm ID×250-length) was used. A continuous electrolytically regenerated packed bed suppressor 22 with two electrode chambers, as described in this disclosure, was used. The body of suppressor 70 consisted of a column (4-mm ID×15-mm length) packed with a porous (45–90 um pore size) sulfonated ion exchange monolith (Dionex Corporation) in hydronium form. A cation exchange membrane AMI-7000 (Membrane International, Glen Rock, N.J.) was used as the barrier 78 in the cathode chamber 74 and the barrier 84 in the anode chamber 80. A Model E3612A DC power supply (Hewlett Packard, Calif.) was used to apply DC voltage to the anode 76 and cathode 82 of the suppressor 70. A Dionex ED40 conductivity detector equipped with a flow-through conductivity cell was used to monitor the effluent from the suppressor.

The eluent generator used was the same one described in Example 1. A Dionex EG40 Eluent Generator Module was used to supply the DC current to the anode and cathode of the eluent generator. A Dionex PeakNet 5.0 computer workstation was used for instrument control, data collection and processing.

FIG. 6 shows the separation of fluoride, chloride, carbonate, sulfate, nitrate and phosphate on the AS15 column using the apparatus illustrated in FIG. 2. In this separation, the eluent generator was used to generate 38 mN KOH at 1.0 mL/min. The current applied to the suppressor was 100 mA and the operating voltage of the device was 20 V.

EXAMPLE 3

This example illustrates the use of the eluent generator of FIG. 1 in combination with a suppressor of the self-regenerating type described in U.S. Pat. No. 5,248,426 for separation of common anions. The major apparatus components are shown in FIG. 3. A DX500 ion chromatographic system (Dionex Corporation, Sunnyvale, Calif.) consisting of a GP40 pump 10, an injection valve 14 and an AS15 separator column (4-mm ID×250-length ) was used. A Dionex ASRS a nion suppressor (P/N 53946) was used as the suppressor. A built-in power supply in a Dionex ED40 detector was used to supply 300 mA of DC current to the suppressor. A Dionex ED40 conductivity detector equipped with a flow-through conductivity cell was used to monitor the effluent from the suppressor.

The eluent generator used was the same one described in Example 1. A Dionex EG40 Eluent Generator Module was used to supply the DC current to the anode and cathode of the eluent generator. A Dionex PeakNet 5.0 computer workstation was used for instrument control, data collection and processing.

FIG. 7 shows the separation of fluoride, chloride, carbonate, sulfate, nitrate and phosphate on the AS15 column using the apparatus illustrated in FIG. 3. In this separation, the eluent generator was used to generate a hydroxide gradient of 1 to 100 mN KOH at 1.0 mL/min. In this set of experiments, the separation of common anions on the AS15 column was performed repeatedly over a period of 43 days, and the effluent leaving the anode chamber was recycled. FIG. 8 shows the stability of retention times of the target anions on the AS-15 column over a total of 980 injection. FIG. 9 shows the conductance profiles of KOH gradients generated by the IRD. The above results show that the apparatus described above can be used to generate highly reproducible KOH gradients (1 to 100 mN at 1.0 mL/min) and to obtain highly reproducible separation of anions.

EXAMPLE 4

This example also illustrates the use of the apparatus of FIG. 3 for cation analysis. A DX500 ion chromatographic system (Dionex Corporation, Sunnyvale, Calif.) consisting of a GP40 pump 110, an injection valve 14 and a CS12A separator column (4-mm ID×250-length) was used. A Dionex CSRS cation suppressor (P/N 53948) was used as the suppressor. A built-in power supply in a Dionex ED40 detector was used to supply 300 mA of DC current to the suppressor. A Dionex ED40 conductivity detector equipped with a flow-through conductivity cell was used to monitor the effluent from the suppressor.

The eluent generator was constructed using an EGC-MSA generator cartridge (P/N 53987, Dionex Corporation, Sunnyvale, Calif.). The parts of the EGC-MSA generator cartridge were used as the anode chamber, anode and the barrier. The EGC-MSA cartridge was fitted with a cathode chamber (1-inch ID×2.5-inch length) made of polypropylene. The cathode chamber was fitted with a perforated platinum electrode as the cathode at its outlet. The ion exchange resin bed in the anode chamber consisted of three sections including a bed (1-inch ID×0.3 inch length) of 200–400 mesh Bio-Rad AG3X4 resin in methansulfonate form, a bed (1-inch ID×0.2 inch length) of 200–400 Dowex 1X8 resin in methansulfonate form and a bed (1-inch ID×2 inch length) of 200–400 Dowex 1X8 resin in methansulfonate form, and a bed (1-inch ID×2 inch length) of Dowex 1X8 resin in hydroxide form. The bed of Bio-Rad AG3X4 resin in methansulfonate form was in direct contact with the barrier. The bed of Dowex 1X8 resin in hydroxide form was in direct contact with the platinum cathode at the chamber outlet. The bed of Dowex 1X8 resin in methansulfonate form was sandwiched between the bed of Bio-Rad AG3X4 resin in methansulfonate form and the bed of Dowex 1X8 resin in hydroxide form. Bio-Rad AG3X4 resin is weakly basic anion exchange resin and was used to stop the migration of hydroxide ions from the cathode to the anode of the eluent generator in order to maintain the current efficiency of the device. A Dionex EG40 Eluent Generator Module was used to supply the DC current to the anode and cathode of the eluent generator. A Dionex PeakNet 5.0 computer workstation was used for instrument control, data collection and processing.

FIG. 10 shows the gradient separation of lithium, sodium, ammonium, potassium, magnesium and calcium ions on the CS12A column using the apparatus described above. In this separation, the eluent generator was used to generate a MSA gradient of 0.5 mN to 60 mN MSA at 1.0 mL/min, and the effluent leaving the cathode chamber was recycled. The results show that the apparatus described above can be used to obtain gradient separation of cations.

EXAMPLE 5

This example illustrates the use of the eluent generator of FIG. 4 in combination with a suppressor of the self-regenerating type described in U.S. Pat. No. 5,248,426 for separation of common anions. The major system components illustrated in FIG. 4. A DX500 ion chromatographic system (Dionex Corporation, Sunnyvale, Calif.) consisting of a GP40 pump, an injection valve and an AS11 separator column (4-mm ID×250-length) was used.

A Dionex ASRS anion suppressor (P/N 53946) was used as the suppressor. A built-in power supply in a Dionex ED40 detector was used to supply 300 mA of DC current to the suppressor. A Dionex ED40 conductivity detector equipped with a flow-through conductivity cell was used to monitor the effluent from the suppressor. The eluent generator was constructed by coupling two Dionex EGC-KOH generator cartridges (one used as the cathode chamber and one used as the anode chamber) using a polypropylene connector (1-inch ID×2.75-inch length). The polypropylene connector served the function of the electrolyte chamber and was filled with an electrolyte solution of 2.0 M $K_2HPO_4$. A Dionex EG40 Eluent Generator Module was used to supply the DC current to the anode and cathode of the eluent generator. A Dionex PeakNet 5.0 computer workstation was used for instrument control, data collection and processing.

FIG. 11 shows the overlay of 12 consecutive separations of five common anions using the non-integrated ion reflux device. The eluent generator was used to generate and recycle 15 mN KOH at 2.0 mL/min (the applied current was 48.2 mA). The results show that the non-integrated ion reflux device can be used to obtain highly reproducible separation of anions.

EXAMPLE 6

In this example, a flow-through sponge-like cation exchange bed is formed to act in place of an ion exchange resin bed as the ion exchange medium in the electrolyte ion reservoir of the present invention.

Styrene and divinylbenzene are copolymerized in the presence of an appropriate catalyst and a porogen. A porogen is an added material which, when removed after the polymerization is complete, creates a macroporosity in the polymerized structure. This porosity should be such that it provides for a ready flow of liquids through the polymer phase while at the same time providing adequate areas of contact between the polymer and liquid phase. The porogen can be a finely divided solid which can be easily removed by dissolution in acid or base (e.g., calcium carbonate or silica), or it can be a solvent which is rejected by the polymer as it forms and is subsequently displaced by another solvent or water. Suitable liquid porogens include an alcohol, e.g., used in the manner described in *Analytical Chemistry*, Vol. 68, No. 2, pp. 315–321, Jan. 15, 1996.

After the porogen is removed, the polymer is sulfonated by commonly known sulfonating agents such as concentrated sulfuric acid or chlorosulfanic acid.

A suitable shape for the polymer is a cylindrical rod which, after sulfonation and conversion to the suitable metal ion form can be placed in the cylindrical cavity of the suppressor column. Preferably, the ion exchange rod is introduced into the column in a slightly shrunken form so that in its typical use environment it swells to form a tight fit with the wall of the column and the cation exchange membrane(s) that separate the ion exchange rod from the electrode compartment(s).

As a final step, the rod is treated so that the part closest to the outlet is in the hydronium form while the part closest to the inlet is in a metal cation form such as the potassium form. This is accomplished by treating the rod with the appropriate amount of acid, or by electrochemically displacing potassium ions with hydronium ions.

What is claimed is:

1. Apparatus for ion analysis comprising:
   (a) a chromatographic separator comprising chromatographic separating medium for separating ionic species of a sample eluted therethrough with an eluent solution comprising an electrolyte including electrolyte ions of opposite charge to said ionic species, said chromatographic separator having an inlet and an outlet,
   (b) a suppressor for treating effluent eluted from said chromatographic separator, said suppressor including
      (1) a chromatography effluent compartment having an inlet and an outlet,
      (2) an ion receiving compartment having an inlet and an outlet,
      (3) at least a first suppressor ion exchange barrier partitioning said chromatography eluent compartment and ion receiving compartment and defining therewith a chromatography effluent flow channel and an ion receiving flow channel, respectively, each having an inlet and an outlet, said first suppressor barrier being preferentially permeable to ions of one charge only, positive or negative, of the same charge as said transmembrane electrolyte ions,
   (c) a detector suitable for detecting separated ionic species having an inlet and an outlet, said detector inlet communicating with said chromatography effluent channel outlet to receive treated chromatography effluent therefrom,
   (d) an eluent generator comprising:
      (1) at least a first generator electrode chamber having an inlet and outlet,
      (2) a first generator electrode disposed in said first generator electrode chamber,
      (3) an electrolyte ion reservoir,
      (4) at least a first charged generator barrier separating said first eluent generator electrode chamber from said electrolyte ion reservoir, said first generator barrier preventing significant liquid flow but permitting transport of said electrolyte ions,
      (5) a second generator electrode in electrical communication with said first electrode through said electrolyte ion reservoir, said second generator electrode being on the opposite side of said first generator barrier from said first generator electrode,
      (6) a first conduit providing fluid communication between said ion receiving compartment outlet and said second generator electrode, and
      (7) a source of aqueous liquid in fluid communication with said first generator electrode chamber inlet, and
   (e) a second conduit providing fluid communication between said first generator electrode chamber outlet and said chromatographic separator inlet.

2. The apparatus of claim 1 in which said eluent generator further comprises
   (8) a second charged generator barrier of the same charge as said first barrier, said second generator barrier being disposed between said second electrode and said electrolyte ion reservoir, thereby forming a second generator electrode chamber, said second generator barrier preventing significant liquid flow but permitting transport of ions of the same charge as said electrolyte ions.

3. The apparatus of claim 2 in which said electrolyte ion reservoir comprises a liquid solution of an electrolyte ion salt or hydroxide, or both.

4. The apparatus of claim 1 further comprising:
(f) a third conduit providing fluid communication between said second generator electrode and said first generator electrode chamber inlet for providing said aqueous liquid source.

5. The apparatus of claim 1 further comprising a polishing column including a charged medium for removing ions, said column being disposed along said second or third conduits.

6. The apparatus of claim 1 in which said electrolyte ion reservoir comprises ion exchange medium including exchangeable transmembrane electrolyte ions.

7. The apparatus of claim 6 in which said electrolytic ion reservoir comprises an ion exchange medium upstream portion and an ion exchange medium downstream portion, said upstream portion comprising a weakly acidic or weakly basic ion exchange material upstream layer of the same charge as said electrolyte ions, not in hydronium ion or hydroxide ion form, and said downstream portion comprising a strongly acidic or strongly basic ion exchange material downstream layer in hydronium or hydroxide form of the same charge as said electrolyte ions.

8. The apparatus of claim 6 in which said upstream portion further comprises an intermediate ion exchange medium layer between said upstream layer and said downstream layer, said intermediate layer comprising a strongly acidic or strongly basic ion exchange material of the same charge as said electrolyte ions not in hydronium ion or hydroxide ion form.

9. The apparatus of claim 1 in which said first conduit is in fluid communication with said electrolyte ion reservoir which is also in fluid communication with said second electrode.

10. The apparatus of claim 1 further comprising flow-through ion exchange matrix with exchangeable ions of the same charge as said electrolyte ions disposed in said chromatography effluent flow channel and a first suppressor electrode disposed in said ion receiving flow channel.

11. The apparatus of claim 1 further comprising a second suppressor electrode chamber having an inlet and an outlet and a second electrode disposed in said second electrode chamber, said first conduit providing fluid communication between said second suppressor electrode chamber outlet and said second generator electrode.

12. The apparatus of claim 11 in which said detector outlet is in fluid communication with said second electrode chamber.

13. The apparatus of claim 1 in which said detector outlet communicates directly or indirectly with said ion receiving flow channel inlet to permit flow of post-detection treated effluent thereto.

14. A method of ionic species analysis comprising:
(a) eluting a sample containing ionic species to be detected in a water-containing eluent solution comprising electrolyte, including electrolyte ions of opposite charge to said ionic species, through a chromatographic separator, having an inlet and an outlet, and comprising chromatographic separation medium in which said ionic species are separated,
(b) flowing the chromatography effluent from said chromatographic separator outlet through a chromatography effluent flow channel of a suppressor in which said chromatography effluent flow channel is separated by an at least a first suppressor ion exchange barrier with exchangeable ions, of the same charge as said electrolyte ions, from an ion receiving flow channel having an inlet and an outlet,
(c) flowing the treated effluent from said chromatography effluent flow channel through a detector in which said separated ionic species are detected.
(d) directing an aqueous liquid through said ion receiving flow channel so that electrolyte ions from the chromatography effluent flowing through said chromatography effluent flow channel are diffused through said first suppressor barrier into said ion receiving flow channel, converting said electrolyte in said chromatography effluent flow channel to weakly dissociated form,
(e) passing an electrical potential between said chromatography effluent flow channel and said first ion receiving flow channel transverse to liquid flow through said chromatography effluent flow channel to assist diffusion of said electrolyte ions through said first suppressor barrier, said ion receiving flow channel being of opposite charge to said electrolyte ions,
(f) directing the effluent from said ion receiving flow channel through an eluent generator including at least a first generator electrode in a first generator chamber separated from an electrolyte ion reservoir by a first generator barrier substantially preventing liquid flow while providing an ion transport bridge for said electrolyte ions, said detector effluent flowing past a second generator electrode in said eluent generator,
(g) flowing an aqueous liquid stream to said first generator electrode chamber inlet,
(h) applying an electrical potential between said first and second electrodes, whereby water in said aqueous liquid adjacent said second electrode is electrolyzed to hydronium ions or hydroxide ions of the same charge as said electrolyte ions to assist the same to migrate toward said first generator barrier and to be transported across the same to a position adjacent said first generator electrode while water in said aqueous liquid adjacent said first electrode in said first generator electrode chamber is electrolyzed to generate hydroxide or hydronium ions of opposite charge to said electrolyte ions to combine therewith to form an acid or base, and
(i) flowing the acid or base generated in said first generator electrode chamber to said chromatographic separator inlet.

15. The method of claim 14 in which the aqueous liquid stream in step (g) flows in a conduit from said second generator electrode to said first generator electrode chamber inlet.

16. The method of claim 15 further comprising removing ions from said aqueous liquid stream.

17. The method of claim 14 in which said eluent generator further includes a second generator barrier of the same charge as said first generator barrier, said second generator barrier being disposed between said second electrode and said electrolyte ion reservoir, thereby forming a second generator electrode chamber, said second generator barrier preventing significant liquid flow but permitting transport of ions of the same charge as said electrolyte ions, said ion receiving flow channel effluent flowing into said second generator electrode chamber.

18. The method of claim 14 in which said electrolyte ion reservoir comprises an aqueous solution of a transmembrane electrolyte ion salt or hydroxide, or both.

19. The method of claim 14 in which said electrolyte ion reservoir comprises ion exchange resin including exchangeable transmembrane electrolyte ions.

20. The method of claim 14 in which said electrolytic ion reservoir comprises an ion exchange medium upstream portion and an ion exchange medium downstream portion, said upstream portion comprising a weakly acidic or weakly basic ion exchange material upstream layer of the same charge as said electrolyte ions, not in hydronium ion or hydroxide ion form, and said downstream portion comprising a strongly acidic or strongly basic ion exchange material downstream layer in hydronium hydroxide form of the same charge as said electrolyte ions.

21. The method of claim 19 in which said upstream portion further comprises an intermediate ion exchange medium layer between said upstream layer and said downstream layer, said intermediate layer comprising a strongly acidic or strongly basic ion exchange material of the same charge as said electrolyte ions not in hydronium ion or hydroxide ion form.

22. The method of claim 19 in which said detector effluent flows through said ion exchange medium and past said second electrode.

23. The method of claim 14 in which a separator bed of ion exchange material with exchangeable ion of the same charge as said electrolyte ions is disposed in said chromatography effluent flow channel and in which said ion receiving flow channel comprises a first suppressor electrode chamber with a first suppressor electrode of opposite charge to said electrolyte ions.

24. The method of claim 23 in which, prior to flowing through said first suppressor electrode chamber, said detector effluent flows through a second suppressor electrode chamber including a second suppressor electrode of opposite charge to that of said electrolyte.

25. The method of claim 14 in which the effluent from said detector comprises the aqueous liquid flowing through said ion receiving flow channel.

* * * * *